United States Patent [19]
Wiggins et al.

[11] Patent Number: 5,827,640
[45] Date of Patent: Oct. 27, 1998

[54] METHODS FOR THE PRESERVATION OF CELLS AND TISSUES USING TRIMETHYLAMINE OXIDE OR BETAINE WITH RAFFINOSE OR TREHALOSE

[75] Inventors: Philippa M. Wiggins; Alexander B. Ferguson; James D. Watson, all of Auckland, New Zealand

[73] Assignee: Biostore New Zealand Limited, Auckland, New Zealand

[21] Appl. No.: 722,306

[22] Filed: Sep. 30, 1996

Related U.S. Application Data

[63] Continuation-in-part of Ser. No. 662,244, Jun. 14, 1996.
[51] Int. Cl.$^6$ ....................................................... A01N 1/02
[52] U.S. Cl. ............................... 435/1.1; 435/1.2; 435/2; 435/1.3
[58] Field of Search ............................. 435/1.1, 1.2, 1.3, 435/2

[56] References Cited

U.S. PATENT DOCUMENTS

| | | | |
|---|---|---|---|
| 4,267,269 | 5/1981 | Grode et al. ................................ | 435/2 |
| 4,380,582 | 4/1983 | Orlando et al. . | |
| 4,476,221 | 10/1984 | Kane et al. . | |
| 4,980,277 | 12/1990 | Junnila . | |
| 5,084,377 | 1/1992 | Rowan et al. ............................. | 435/1 |
| 5,200,398 | 4/1993 | Strasberg et al. . | |
| 5,242,792 | 9/1993 | Rudolph et al. . | |
| 5,571,801 | 11/1996 | Segall et al. ............................. | 514/59 |

FOREIGN PATENT DOCUMENTS

| | | | |
|---|---|---|---|
| 9003310 | 1/1992 | Brazil .............................. | A01N 1/02 |
| 0259739 | 3/1988 | European Pat. Off. .......... | C12N 1/04 |
| 0306132 | 3/1989 | European Pat. Off. ......... | A01N 1/02 |
| 0556096 | 8/1993 | European Pat. Off. .......... | A61L 2/04 |
| 228439 | 10/1985 | German Dem. Rep. . | |
| 3625170 | 7/1987 | Germany .......................... | C12N 1/04 |
| 6293602 | 10/1994 | Japan ............................... | A01N 3/00 |
| 9118504 | 12/1991 | WIPO .............................. | A01N 1/02 |
| 9203046 | 3/1992 | WIPO .............................. | A01N 1/02 |
| 9218136 | 10/1992 | WIPO ............................ | A61K 31/70 |
| 9314191 | 7/1993 | WIPO .............................. | C12N 5/00 |
| 9429691 | 12/1994 | WIPO .............................. | G01N 1/00 |

OTHER PUBLICATIONS

Molinia et al., Effect of monosaccharides and disaccharides in Tris–based diluents on motility, acrosome integrity and fertility of pellet frozen ram spermatozoa., *Animal Reproduction Sci. 36*, 113–122, 1994.

Yano et al., Butyrate increases catalase activity and protects rat pulmonary artery smooth muscle cells against hyperoxia, *Biochem. and Biophys. Research Commun 164*(3), 1143–1148, 1989.

Staecker et al., Sodium butyrate preserves aspects of the differentiated phenotype of normal adult rate hepatocytes in culture, *Journal of Cellular Physiology 135*, 367–376, 1988.

Park et al., Effects of Cryoprotectants in minimizing physiochemical changes of bovine natural actomyosin during frozen storage, *J. Food Biochem 11*(2), 143–161, 1987.

Boutron et al., Reduction in Toxity for Red Blood Cells in Buffered Solutions containing high Concentrations of 2.3–Butanediol by Trehalose, Sucrose, Sorbitol or Mannitol, *Cryobiology 31*(4), 367–373, 1994.

Karow et al., Effects of Temperature, Potassium Concentration, and Sugar on Human Spermatozoa Motility: A Cell Preservation Model from Reproductive Medicine, *Cryobiology 29*, 250–254, 1992.

Newman et al., The Role of Trehalose and other Carbohydrates in Biopreservation, *Biotechnology and genetic engineering reviews 11*, 263–294, 1993.

Hogman et al., Red Cell Preservation in Protein–Poor Media, *Vox Sanguinis 41*, 274–281, 1981.

Stibenz, Preservation of Resuspended Red Cell Concentrates, Rate of Vesiculation and of Spontaneous Hemolysis, *Folia haematologica. Internationales magazin fur klinische und morphologische hamatologie 114*(4), 469–470, 1987.

Shier, Studies on the Mechanisms of Mammalian Cell Killing by a Freeze–Thaw Cycle: Conditions that Prevent Cell Killing Using Nucleated Freezing, *Cryobiology 25*, 110–120, 1988.

Brearley et al., A comparative study of the cryopreservation of human erythrocytes, ghosts and liposomes, *Biochemical Society Transaction 16*, 354, 1988.

Goldstein et al., Enhanced transfection efficiency and improved cell survival after electroporation of G2/M–synchronized cells and treatment with sodium butyrate, *Nucleic acid res. 17*(10), 3959–71, 1989.

Fabre et al., Effects of different substances (sucrose, glucose, sorbitol and mannitol) on the resistance to deep freezing in liquid nitrogen of meristems from in vitro cultured carnations, *Comptes rendus de l'Academie des Sciences Serie III, Sciences de la vie 304*(20), 507–510. 1987.

Brass et al., Evaluation of University of Wisconsin Cold–Storage Solution in Warm Hypoxic Perfusion of Rat Liver: the Addition of Fractose Reduces Injury, *Gastroenterology 105*(5), 1455–1463, 1993.

(List continued on next page.)

*Primary Examiner*—Sandra E. Saucier
*Attorney, Agent, or Firm*—Janet Sleath; Ann W. Speckman

[57] ABSTRACT

The present invention provides solutions and methods for preserving biological material that enable organs, tissues and cells to be stored for extended periods of time with minimal loss of biological activity. The inventive solutions are substantially isotonic with the biological material to be preserved and are substantially free of univalent oxyanions and of iodide. The solutions comprise a first neutral solute having a molecular weight of at least about 335 and a solubility in water of at least about 0.3M, and a second neutral solute having a molecular weight of less than about 200 and having both hydrophilic and hydrophobic moieties. The inventive solutions preferably contain $CaSO_4$, together with combinations of anions and cations from the protein-stabilizing ends of the Hofmeister series, such as $K_2SO_4$. In particular methods using solutions comprising raffinose or trehalose and trimethyl amine oxide or betaine, wherein the solution is substantially isotonic with the biological material and the solution is substantially free of iodide, dihydrogen phosphate, bicarbonate, nitrate and bisulfate are described.

23 Claims, 26 Drawing Sheets

OTHER PUBLICATIONS

Fremes et al., Cardiac Storage with UW Solution and Glucose, *The Annals of thoracic surgery 58*(5), 1368–1372, 1994.

Eschwege et al., Successful–4° C. Liver Preservation in Rats with University of Wisconsin Solution and 2–3–Butanediol, *Transplantation Proceedings 27*(4), 2514–2515, 1995.

Minor et al., Effects of taurine on liver preservation in UW solution with consecutive ischemic rewarming in the isolated perfused rate liver, *Transplantation international 8,* 174–179, 1995.

Ahmad et al., Deep Freezing of Buffalo Bull Semen of Nili–ravi Breed, *Indian Journal of Animal Health 22*(2), 111–114, 1983.

Shier et al., Isotonic sucrose improves cryopreservation of cultured mammalian cells, *In Vitro Cell Devel. Biol. 31,* 336–337, 1995.

Strauss et al., SAG–sucrose medium for red blood cell preservation, *Biomed. Biochem, Acta 46,* S295–299, 1987.

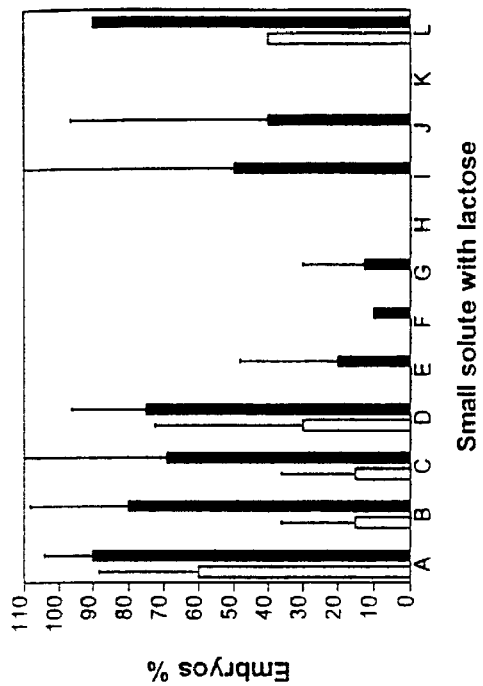
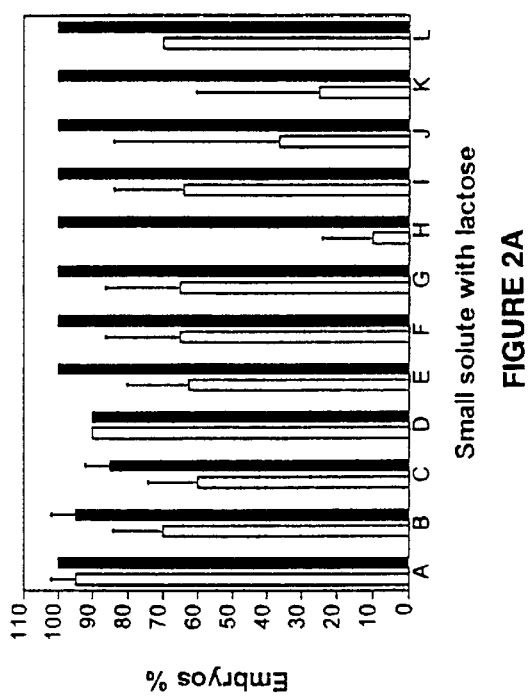
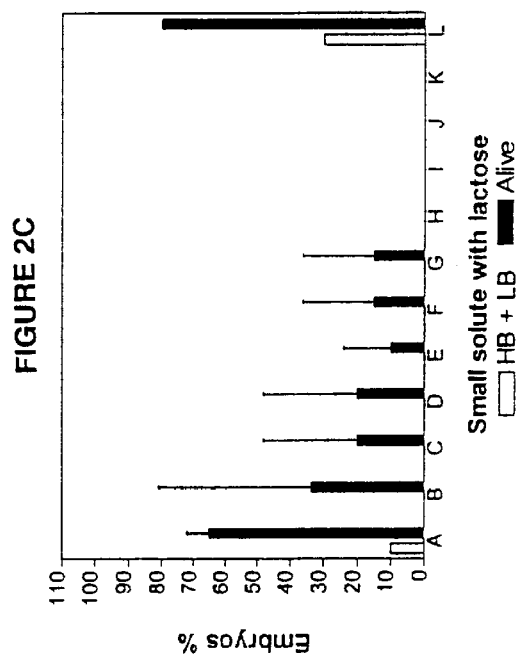
FIGURE 2A
FIGURE 2B
FIGURE 2C
A = TMAO
B = betaine
C = sarcosine
D = glucose
E = mannose
F = fructose
G = galactose
H = ribose
I = sorbitol
J = inositol
K = taurine
L = PBS A = TMAO
B = betaine
C = sarcosine
D = glucose
E = mannose
F = fructose
G = galactose
H = ribose
I = sorbitol
J = inositol
K = taurine
L = PBS A = TMAO
B = betaine
C = sarcosine
D = glucose
E = mannose
F = fructose
G = galactose
H = ribose
I = sorbitol
J = inositol
K = taurine
L = PBS ☐ HB + LB    ■ Alive

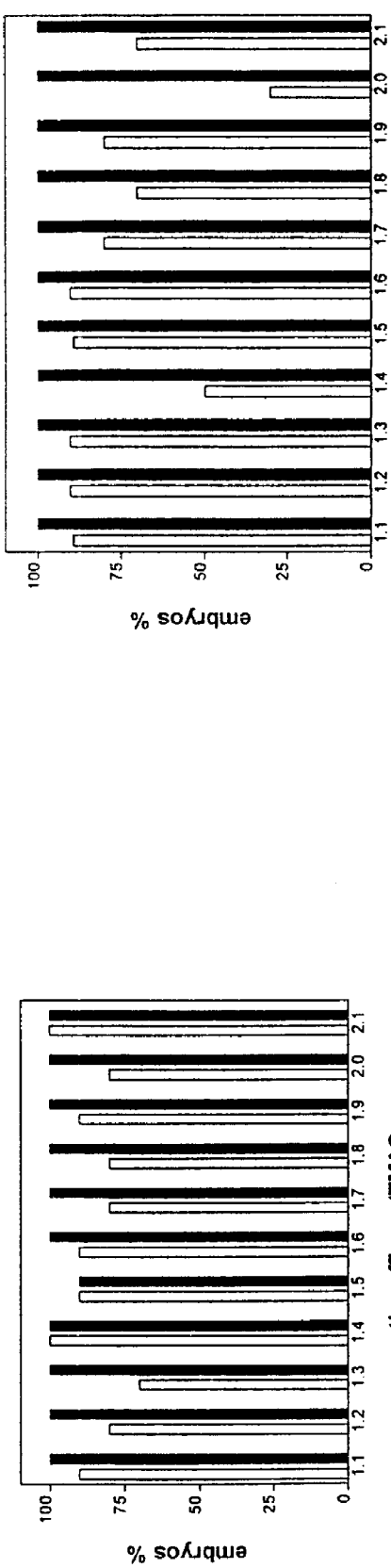
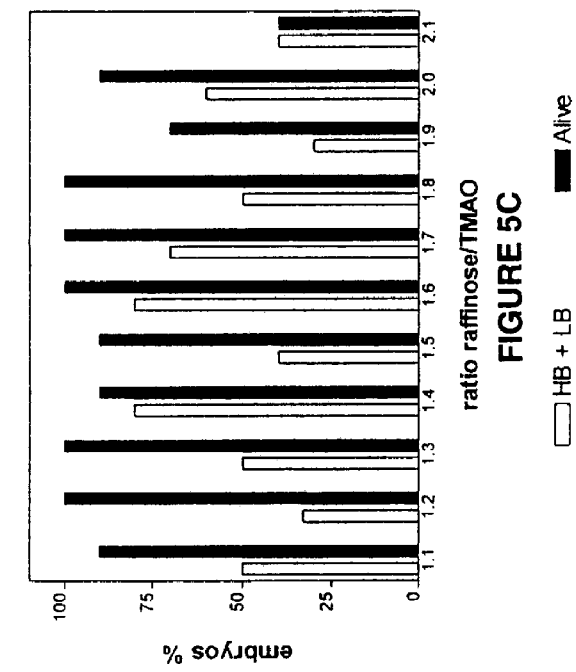
FIGURE 5A
FIGURE 5B
FIGURE 5C

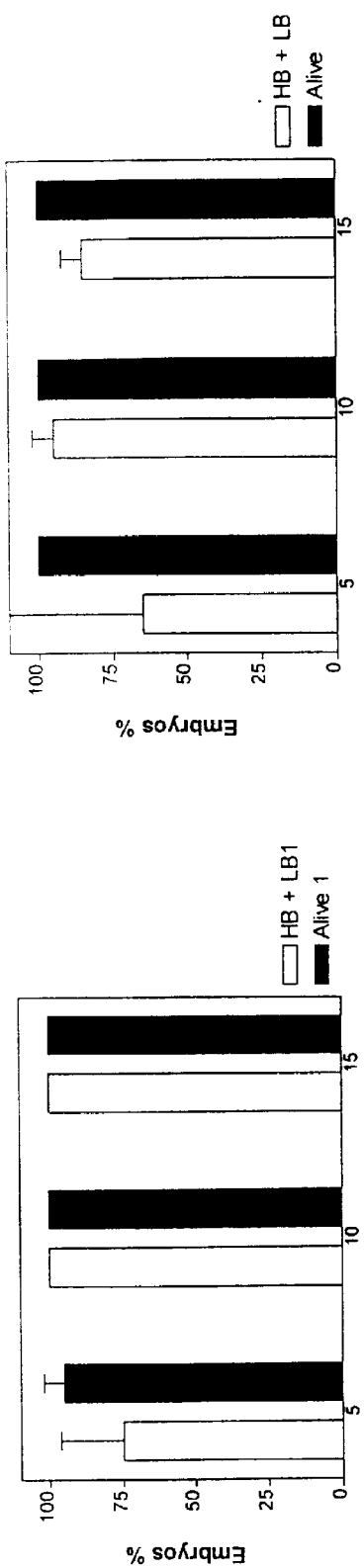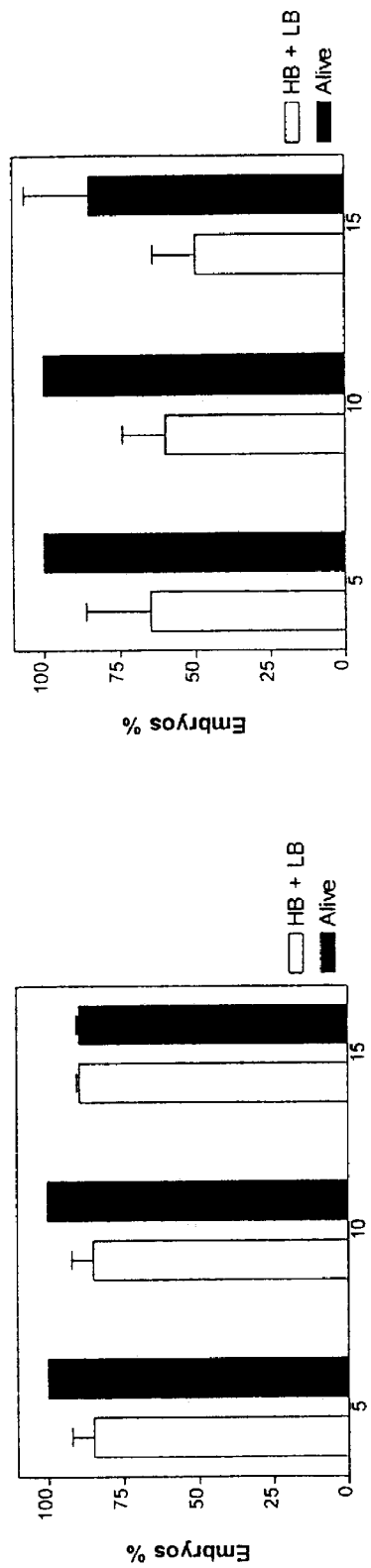
FIGURE 10A
FIGURE 10B
FIGURE 10C
FIGURE 10D

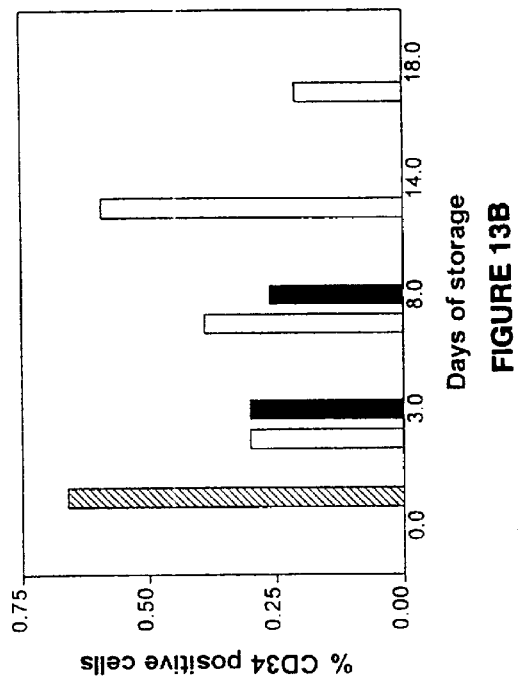
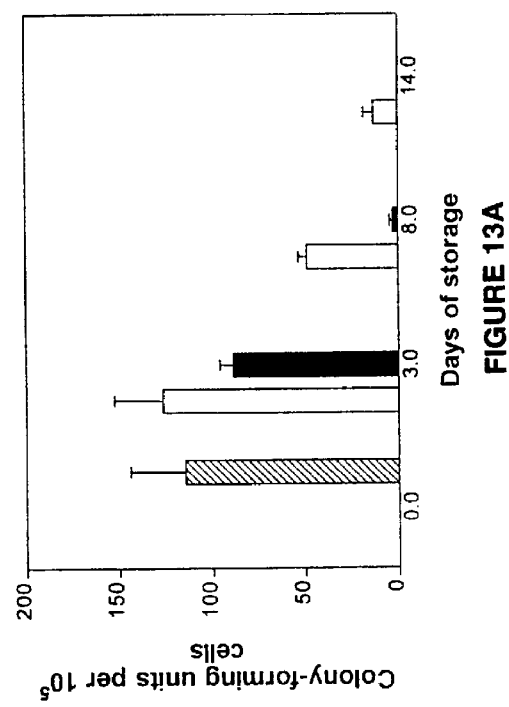
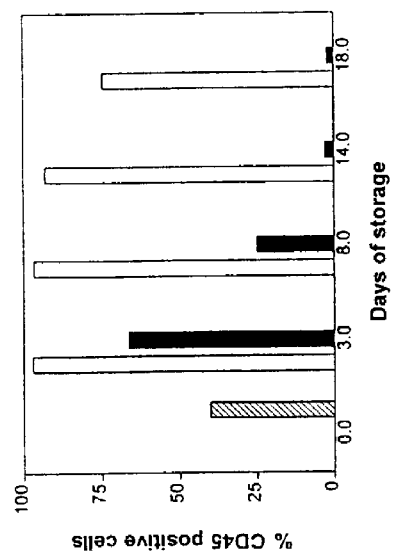
FIGURE 13A
FIGURE 13B
FIGURE 13C
☐ raffinose/TMAO (ratio 1.6:1); 1.75 mM CaSO₄; 0.29 OsM
■ M-2, a Hepes-buffered balanced saline medium PBS = phosphate-buffered saline; B = betaine; G = galactose; S = sorbitol; M = mannose; t = trehalose; R = raffinose; R/T = raffinose/TMAO (ratio 1.6:1); R/B = raffinose/betaine (ratio 1.6:1); t/T = trehalose/TMAO (ratio 1.6:1); t/B = trehalose/betaine (ratio 1.6:1)

METHODS FOR THE PRESERVATION OF CELLS AND TISSUES USING TRIMETHYLAMINE OXIDE OR BETAINE WITH RAFFINOSE OR TREHALOSE

REFERENCE TO RELATED APPLICATIONS

This application is a continuation-in-part of U.S. application Ser. No. 08/662,244, filed Jun. 14, 1996.

TECHNICAL FIELD OF THE INVENTION

This invention relates to the field of preservation of biological materials and, more particularly, to compositions and methods for the preservation of organs, tissues and cells from mammals, marine organisms and plants.

BACKGROUND OF THE INVENTION

Methods for the preservation of biological materials are employed in many clinical and veterinary applications wherein living material, including organs, tissues and cells, is harvested and stored in vitro for some period of time before use. Examples of such applications include organ storage and transplants, autologous and allogeneic bone marrow transplants, whole blood transplants, platelet transplants, embryo transfer, artificial insemination, in vitro fertilization, skin grafting and storage of tissue biopsies for diagnostic purposes. Preservation techniques are also important in the storage of cell lines for experimental use in hospital, industrial, university and other research laboratories.

Methods currently employed for the preservation of cellular biological materials include immersion in saline-based media; storage at temperatures slightly above freezing; storage at temperatures of about −80° C.; and storage in liquid nitrogen at temperatures of about −196° C. The goal of these techniques is to store living biological materials for an extended period of time with minimal loss of normal biological structure and function.

Storage of organs, such as heart and kidneys, at temperatures below 0° C. frequently results in the loss of many cells with a corresponding reduction in viability of the organ. Such complex biological materials are therefore typically stored in aqueous, saline-based media at temperatures above freezing, typically around 4° C. Saline-based media typically consist of isotonic saline (sodium chloride 0.154M) which has been modified by the addition of low concentrations of various inorganic ions, such as sodium, potassium, calcium, magnesium, chloride, phosphate and bicarbonate, to mimic the extracellular environment. Small amounts of compounds such as glucose, lactose, amino acids and vitamins are often added as metabolites. All saline-based media used for preservation of biological materials have high electrical conductivity. Examples of media currently employed for the preservation of biological materials include phosphate-buffered saline (PBS), M-2 (a Hepes buffered murine culture medium), Ringer's solution and Krebs bicarbonate-buffered medium.

The viability of biological materials stored in saline-based media gradually decreases over time. Loss of viability is believed to be due to the build-up of toxic wastes, and loss of metabolites and other supporting compounds caused by continued metabolic activity. Using conventional saline-based media, living tissues can only be successfully preserved for relatively short periods of time. Examination of the microstructure of organs stored towards the upper limit of time shows degeneration, such as of mitochondria in heart muscle, and the performance of the organ once replaced is measurably compromised. For example, a human heart can only be stored in cold ionic solutions for about 5 hours following removal from a donor, thereby severely limiting the distance over which the heart can be transported.

When employing freezing techniques to preserve biological materials, cryoprotectants, such as glycerol, dimethylsulfoxide (DMSO), glycols or propanediol, are often introduced to the material prior to freezing in order to limit the amount of damage caused to cells by the formation of ice crystals during freezing. The choice and concentration of cryoprotectant, time-course for the addition of cryoprotectant and temperature at which the cryoprotectant is introduced all play an important role in the success of the preservation procedure. Furthermore, in order to reduce the loss of cells, it is critical that such variables as the rate and time-course of freezing, rate and time-course of thawing and further warming to room or body temperature, and replacement of cryoprotectant solution in the tissue mass with a physiological saline solution be carefully controlled. The large number of handling steps required in freezing techniques increases the loss of cells. The freezing techniques currently employed in the preservation of biological materials are both technically demanding and time consuming. Other disadvantages of preserving biological materials by freezing include: reduction of cell viability; potential toxic effects of the cryoprotectant to the patient upon re-infusion; and the high costs of processing and storage.

As an example, cryopreservation, generally including the addition of DMSO as a cryoprotectant, is presently used to store bone marrow harvested for use in transplantation procedures following, for example, high dose chemotherapy or radiotherapy. In autologous transplants the bone marrow must be preserved for prolonged periods, ranging from weeks to months. However, this technique results in significant reduction of stem cell recovery, to levels as low as 50% or less. An additional disadvantage of this technique is that significant damage to various mature cells can occur, thereby requiring further processing to remove these cells prior to freezing. Finally, the use of DMSO results in moderate to severe toxicity to the patient on re-infusion of the preserved bone marrow.

There thus remains a need in the art for improved methods for the preservation of living biological materials.

SUMMARY

The present invention provides compositions and methods for preserving biological materials that enable materials including organs, tissues and cells to be stored for extended periods of time with minimal loss of biological activity.

In one aspect, the present invention provides methods for preserving the viability of biological materials, comprising (a) contacting the biological material with a solution, the solution being substantially isotonic with the biological material and being substantially free of univalent oxyanions and of iodide; and (b) maintaining the biological material at a temperature of less than about 0° C. Preferably the biological material is maintained at a temperature of between −4° C. and about −80° C., most preferably at a temperature of about −80° C.

In one embodiment, the solution in which the biological material is maintained includes a first neutral solute with no net charge, having a molecular weight of at least about 335 and a solubility in water of at least about 0.3M; and a second neutral solute having a molecular weight of less than about 200, the second solute additionally having both hydrophilic and hydrophobic moieties.

Preservation solutions of the present invention may also include one or more ions. A calcium salt, preferably $CaSO_4$ or $CaCl_2$, is used at concentrations of below about 2 mM in many types of preservation solutions. Additional ions may be selected according to their characteristic position in the Hofmeister series of anions or cations. Specifically, ions from the protein-stabilizing ends of the Hofmeister series may be included in the preservation solutions of the present invention. Appropriate ions and selection criteria are described in detail below.

In a preferred embodiment, the first neutral solute is either a disaccharide or a trisaccharide, preferably selected from the group consisting of raffinose, trehalose, sucrose, lactose and analogs thereof. The analogs may be either naturally occurring or synthetic. The second neutral solute is preferably selected from the group consisting of trimethyl amino oxide (TMAO), betaine, taurine, sarcosine, glucose, mannose, fructose, ribose, galactose, sorbitol, mannitol, inositol and analogs thereof. The preservation solutions employed in the inventive methods may also comprise sodium sulfate and calcium, the calcium preferably being present as calcium sulfate at a concentration of about 1.5 mM to about 2.0 mM, most preferably about 1.75 mM.

While the preferred solution for the preservation of a biological material will depend upon the specific biological material to be preserved, it has been found that solutions comprising either raffinose and TMAO, or trehalose and TMAO are particularly efficacious in the preservation of many biological materials. In one embodiment, the inventive solutions comprise raffinose and TMAO in a ratio of about 1.1 to 1 to about 2.0 to 1, preferred about 1.4:1 to about 1.8:1, most preferably 1.6:1. Preferably, the solutions of the present invention comprise between about 60% and about 80% raffinose and TMAO, between about 40% and about 20% sodium sulfate, and between about 1.5 mM and about 2.0 mM calcium sulfate, the raffinose and TMAO being present in a ratio of about 1.6:1. Most preferably, the solution comprises about 70% raffinose and TMAO, about 30% sodium sulfate and about 1.75 mM calcium sulfate, the raffinose and TMAO being present in a ratio of about 1.6:1.

In yet another aspect, a method for the treatment of leukemia is provided, the method comprising removing bone marrow from a patient, contacting the bone marrow with a preservation composition or solution of the present invention for a period of at least about 3 days at a temperature of less than about 0° C., more preferably between about −4° C. and about −80° C., and most preferably at a temperature of about −80° C., in order to purge the bone marrow of leukemic cells, and returning the purged bone marrow to the patient.

As detailed below, it has been found that the solutions and methods of the present invention can be employed to maintain the viability of biological materials, including cells, tissues and organs, for longer periods of time than are generally possible with conventional preservation methods, thereby providing improved storage and transport times for biological materials for use in applications such as organ transplants and bone marrow transplants.

The preservation methods of the present invention are less complex than many of the methods typically employed for the preservation of biological materials, thereby reducing costs and increasing the ease of use and availability of preservation procedures. Furthermore, the inventive compositions are of low toxicity, resulting in fewer negative side effects when biological materials, such as transplant organs, are returned to a patient.

The above-mentioned and additional features of the present invention and the manner of obtaining them will become apparent, and the invention will be best understood by reference to the following more detailed description, read in conjunction with the accompanying drawings.

BRIEF DESCRIPTION OF THE DRAWINGS

FIGS. 2A, B and C illustrate the survival of mouse embryos following 1, 2 and 3 days of storage, respectively, at 4° C. in an aqueous solution of lactose and various Class II solutes, together with 1.75 mM $CaSO_4$.

FIGS. 5A, B and C illustrate the survival of mouse embryos after storage for 1, 2 and 3 days, respectively, at 4° C. in aqueous solutions with varying molar ratios of raffinose to TMAO, with 1.75 mM $CaSO_4$.

FIGS. 10A, B, C and D show the survival of mouse embryos after storage in Solution 70/30 for 1, 2, 3 and 4 days following pretreatment with 25 mM sodium butyrate in PBS for 5, 10, or 15 minutes.

FIGS. 13A, B and C show the percentage of colony forming units, CD34- and CD45-positive cells, respectively, in bone marrow from patient 2 following storage in either raffinose/TMAO with 1.75 mM $CaSO_4$ or in M-2 at 4° C.

DETAILED DESCRIPTION

Figure 1A:
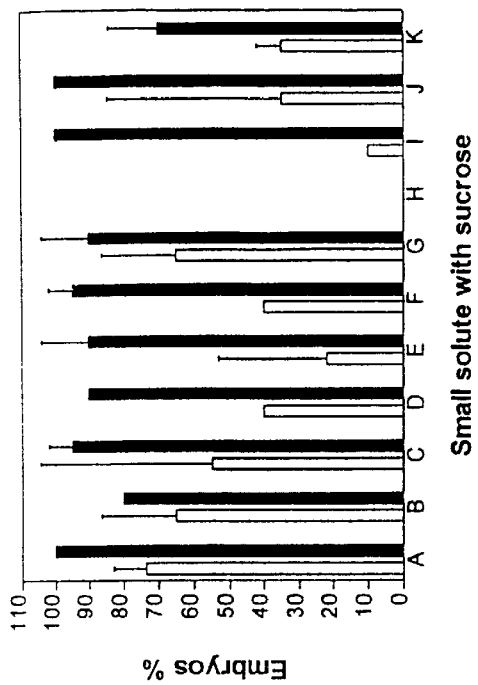
FIGS. 1A, B and C illustrate the survival of mouse embryos following 1, 2 and 3 days of storage, respectively, at 4° C. in an aqueous solution of sucrose and various Class II solutes, together with 1.75 mM $CaSO_4$.
Figure 1B:
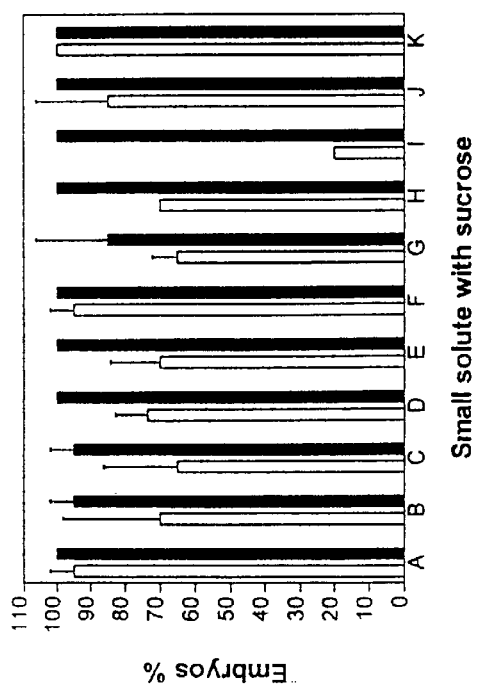
Figure 1C:
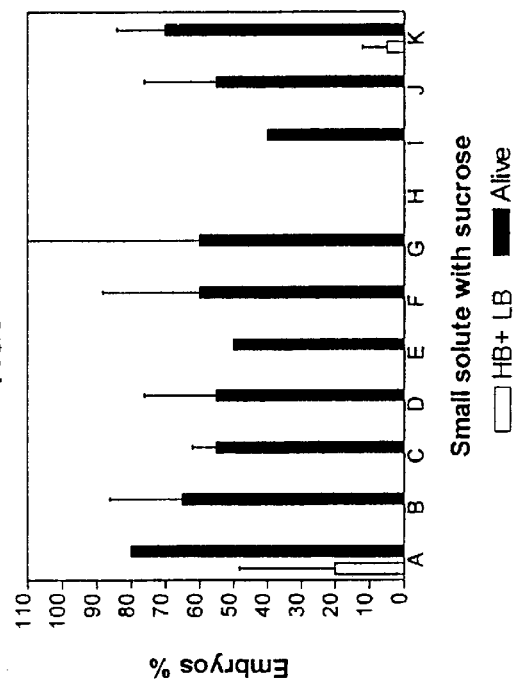
Figure 3B:
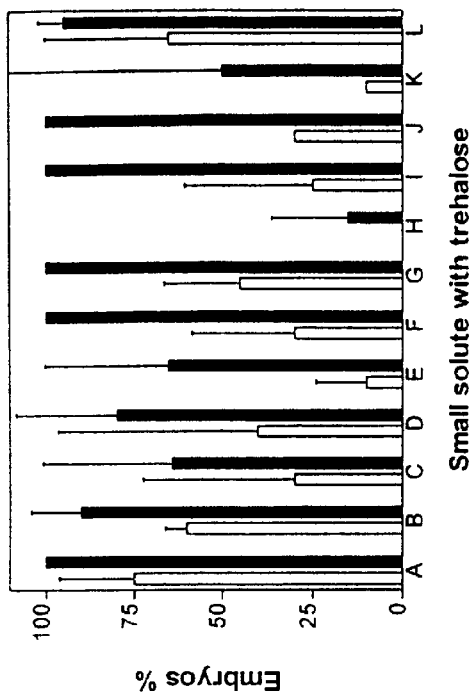
FIGS. 3A, B and C illustrate the survival of mouse embryos following 1, 2 and 3 days of storage, respectively, at 4° C. in an aqueous solution of trehalose and various Class II solutes, together with 1.75 mM $CaSO_4$.
Figure 3A:
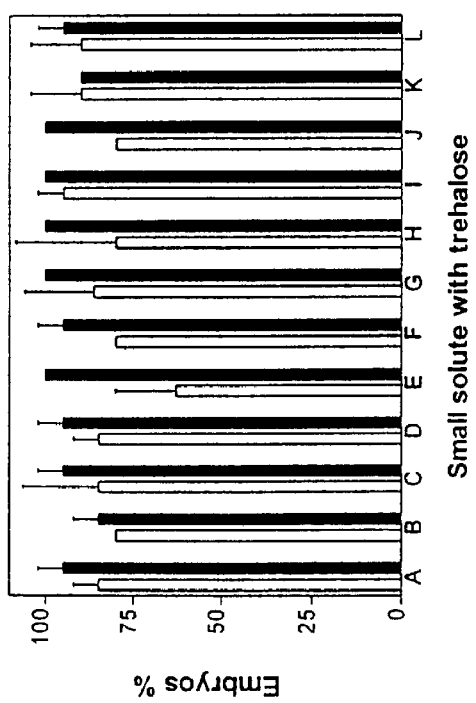
Figure 3C:
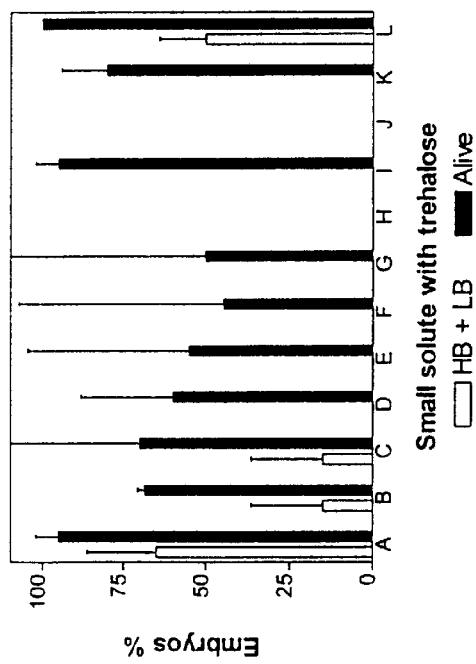
Figure 4A:
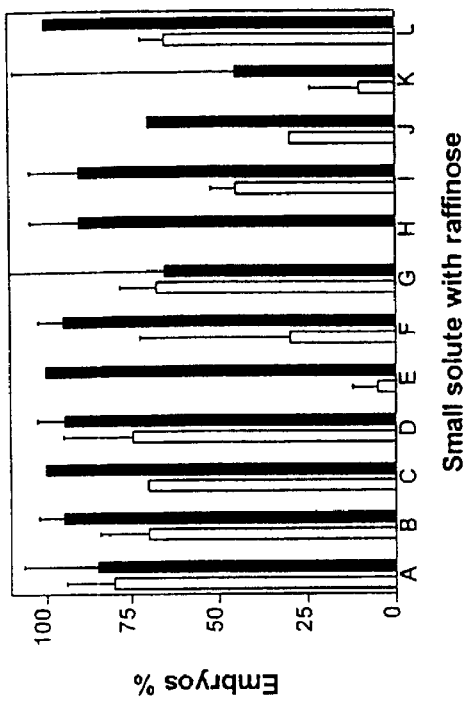
FIGS. 4A, B and C illustrate the survival of mouse embryos following 1, 2 and 3 days of storage, respectively, at 4° C. in an aqueous solution of raffinose and various Class II solutes, together with 1.75 mM $CaSO_4$.
Figure 4B:
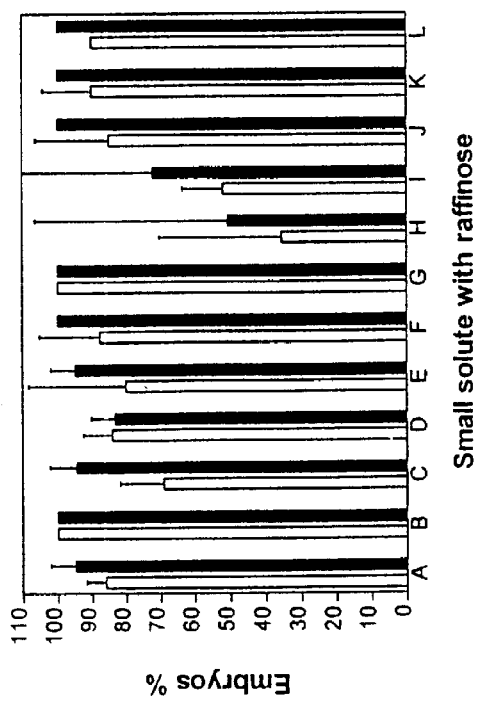
Figure 4C:
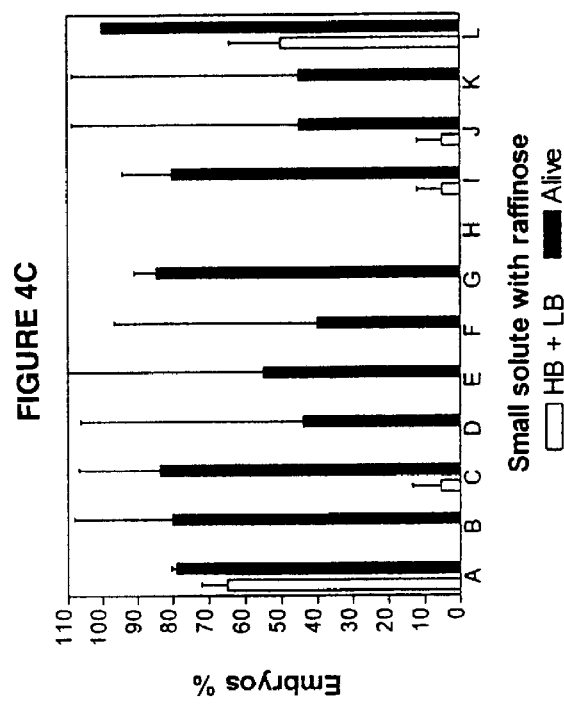

The solutions and methods of the present invention may be used in the preservation of biological materials including mammalian, plant and marine cells, cell lines, tissues and organs. When a biological material is preserved, its viability is maintained in vitro for an extended period of time, such that the material resumes its normal biological activity on being removed from storage. During storage the biological material is thus maintained in a reversible state of dormancy, with metabolic activity being substantially lower than normal. For example, hearts are observed to stop beating during storage. Examples of mammalian biological materials which may be preserved using the present invention include organs, such as heart; cells and tissues such as haematopoietic stem cells, bone marrow, embryos, platelets, osteoblasts, spermatozoa; and various animal cell lines established in tissue culture. In addition to the preservation of human biological materials, the inventive solutions and methods may also be employed in veterinary applications, and for preservation of plant tissues.

The preservative solutions of the present invention may be in either a ready-to-use form or may be provided in a concentrated form, such as a solid, including for example, powder or tablets, which is reconstituted in water prior to use. The inventive solutions may also be provided in a concentrated liquid form for dilution by the user. As with conventional preservative solutions, the inventive solutions are sterile.

The solutions of the present invention are substantially isotonic with the biological material to be preserved. Cells in an isotonic solution neither shrink nor swell substantially. While the preservative solutions of the present invention may have an osmolality substantially equal to that of the biological material to be preserved, this is not a requirement of the inventive solutions, since some solutions may include one or more components which raise the osmolality of the solution but are able to cross semipermeable membranes freely, thus raising the osmotic pressure equally on both sides of the cell membrane.

As detailed below, it has been determined that an osmolality of between about 0.28 OsM and about 0.32 OsM is preferable for solutions for the preservation of mammalian biological materials. Osmolalities of between about 0.9 to about 1.0 OsM and between about 70 to about 80 mOsM are preferred for the preservation of marine and plant biological materials, respectively.

It has been observed that contamination with univalent oxyanions, such as $H_2PO_4^-$, $HCO_3^-$, $NO_3^-$ and $HSO_4^-$, increases the level of metabolic activity during storage. For example, contamination with $HSO_4^-$ was observed to allow a rat heart to beat slowly and feebly, whereas in the absence of univalent oxyanions, no beating occurs. For most applications, preservative solutions of the present invention preferably reversibly depress the level of metabolic activity during storage, and preferably exclude univalent oxyanions.

The inventive solutions comprise a first neutral solute having a molecular weight of at least about 335 and a solubility in water of at least about 0.3M (hereinafter referred to as Class I solutes), and a second neutral solute having a molecular weight of less than about 200 (hereinafter referred to as Class II solutes), the second neutral solute additionally having both hydrophilic and hydrophobic moieties. Class I solutes are generally too large to penetrate cell membranes and act primarily to raise the osmolality of the inventive solutions. Preferably, Class I solutes are disaccharides or trisaccharides. Examples of such solutes include raffinose, trehalose, sucrose, lactose and synthetic or naturally occurring analogs thereof, with raffinose and trehalose being preferred Class I solutes. Class II solutes generally do not passively cross cell membranes, but may be actively taken up by cells in response to an osmotic insult. They are used by many cells as intracellular osmolytes. Examples of such solutes include TMAO, betaine, taurine, sarcosine, glucose, mannose, fructose, ribose, galactose, sorbitol, mannitol and inositol and synthetic or naturally occurring analogs thereof. TMAO is the preferred Class II solute for many biological materials. Solutions comprising either raffinose and TMAO, preferably in a molar ratio of between about 1.1 to 1 to about 2.0 to 1, more preferably between about 1.4:1 to about 1.8:1, most preferably about 1.6:1, or trehalose and TMAO, preferably in a molar ratio of between about 1.1:1 and about 1.4:1, most preferably about 1.3:1, have been found to be particularly useful for the preservation of biological materials.

The inventive solutions may additionally contain one or more ions but are substantially free of univalent oxyanions and iodide. A calcium salt, such as $CaSO_4$, is used at concentrations below about 2 mM in preservation solutions for many applications. Other ionic species may be selected according to their characteristic position in the Hofmeister series of anions and/or cations. The Hofmeister series of anions and cations are ranked in order of decreasing stabilization of protein and membranes (Hofmeister, F., On the understanding of the effect of salts. Second report. On regularities in the precipitating effects of salts and their relationship to their physiological behavior. *Naunyn-Schmiedebergs Archiv fuer Experimentalle Pathologic und Pharmakologic.* (Leipzig) 14:247–260, 1988; Collins, K. D. and Washabaugh, M. W., The Hofmeister effect and the behavior of water at interfaces. *Quarterly. Rev. Biophys.* 18:323–422, 1985). The rank order of anions is: citrate>acetate>dihydrogen phosphate>sulfate>hydroxyl>fluoride>chloride>bromide> iodide>hydrogen phosphate>bicarbonate >bisulfate>nitrate. The rank order of cations is: tetramethyl ammonium>ammonium>cesium>rubidium>potassium> sodium>lithium>calcium>magnesium.

Ions, excluding univalent oxyanions and iodide, may be included in preservation solutions of the present invention at concentrations of less than about 2 mM without regard to their rank order. At ionic concentrations of greater than about 2 mM, the following selection criteria apply:

(i) each anion to the left of chloride is combined in a neutral salt with sodium or a cation to the left of sodium;

(ii) anions to the right of chloride are excluded; and (iii) cations to the right of sodium can be combined only with chloride.

Especially preferred ions for use in preservation solutions include: potassium, tetramethyl ammonium, ammonium, cesium and citrate. Magnesium is also a preferred cation at concentrations of less than about 2 mM.

As detailed below, it has been determined that, with the exception of platelets, effective storage times for biological materials increase with the addition of calcium to the preservative compositions. This may be due to the ability of calcium to stabilize phospholipid bilayers found in cell membranes and to stabilize intercellular adhesion. Preferably the calcium is present as calcium sulfate and is present at a concentration of between 1.5 mM and about 2.0 mM, most preferably 1.75 mM. The addition of sodium sulfate also increases effective storage times for many biological materials. A composition comprising between about 60% and about 80%, preferably about 70%, raffinose and TMAO, between about 40% and about 20%, preferably about 30% sodium sulfate, and about 1.75 mM calcium sulfate, with the raffinose and TMAO being present in a ratio of about 1.6:1 has been found to be particularly effective in preserving many biological materials.

Other components which may be included in the inventive compositions include antibiotics for the control of microorganisms, and proteins, such as bovine serum albumin, for inhibiting the attachment of the biological material, such as embryos, to surfaces. For certain applications, such as storage of hearts, the preservative solution may be saturated with oxygen before use.

While not wishing to be bound by theory, the inventors believe that the preservative solutions of the present invention isolate cells from external stimulatory signals carried through the cell membrane by preventing the opening of ion channels, thereby maintaining the cells in a state of dormancy.

Biological materials to be preserved are harvested using standard techniques and contacted, preferably immersed, in an aqueous preservative solution of the present invention. The biological material may be rinsed with the preservative solution prior to immersion, if required. While the biological materials may be stored at temperatures below freezing, materials are conveniently stored at temperatures of about 4° C. After storage, the preservative solution may be removed from the material and replaced with a standard saline-based medium or the stored material may be used directly in its preservative solution. When the biological material is stored at temperatures below freezing, an effective concentration of a cryoprotectant may be added to the preservative solution, as employed in techniques well known to those of skill in the art. The inventive solutions may thus be used for either long term or short term storage of biological materials.

As detailed below in Example 2, storage times for some biological materials, such as embryos, may be increased by pretreatment with either a Class II solute or sodium butyrate.

The word "about," when used in this application with reference to temperature (0° C.), contemplates a variance of up to 20° from the stated temperature. The word "about," when used in this application with reference to molecular weight, contemplates a variance of up to 10% from the stated molecular weight. The word "about," when used with reference to the solubility of a solute or molarity of a solution, contemplates a variance of up to 0.4 mM from the stated molarity. The word "about," when used with reference to a ratio, contemplates a variance of up to 0.2 on either side of the ratio. The word "about," when used with reference to a percentage solution composition, contemplates a variance of up to 10% from the stated percentage.

The following examples are offered by way of illustration and not by way of limitation.

EXAMPLE 1

The efficacy of the solutions of the present invention in the preservation of mouse embryos was tested as described below. As embryos consist of rapidly dividing cells, they are difficult to arrest, and therefore, provide a sensitive test of storage solutions. Embryos also have the advantage that survival in storage can be assessed after 1–5 days by their ability to hatch in subsequent culture.

Viable mouse embryos were stored for periods of 1, 2 or 3 days at 4° C. in either PBS or an aqueous solution of either raffinose, trehalose, sucrose or lactose (Class I solutes), together with a solute selected from the group consisting of trimethyl amine oxide (TMAO), betaine, taurine, sarcosine, glucose, mannose, fructose, ribose, galactose, sorbitol, mannitol, inositol and taurine (Class II solutes), at a ratio of Class I solute to Class II solute of 1.6:1. Each Class I/Class II solution also contained calcium sulfate at a concentration of 1.75 mM. The solutions also contained 0.1–1% bovine serum albumin (BSA) and 25 mg/L of kanamycin sulfate. All reagents were obtained from Sigma Chemical Company (St. Louis, Mo.). Survival of the embryos was assessed by subsequent culture in Dulbecco's Modified Eagles Medium (DMEM, Life Technologies, Grand Island, N.Y.) and was expressed both as the number of live embryos present after storage and the number of embryos which hatched after 48 hours in culture at 37° C.

The results of these experiments for solutions of sucrose, lactose, trehalose and raffinose are shown in FIGS. 1–4, respectively, wherein HB+LB represents the percentage of embryos hatched or reaching the late blastocyst stage. A significant percentage of embryos hatched following storage for one day in most combinations of solutes, but following three days of storage a high percentage of hatching was only obtained with combinations of raffinose, trehalose or sucrose with TMAO. Raffinose was found to be the best Class I solute and TMAO the best Class II solute, with trehalose and betaine being the second best Class I and Class II solutes, respectively. The optimal total osmolality of the Class I/Class II solutions for preservation of mouse embryos was found to be 0.30 OsM.

The three best combinations of Class I and Class II solutes were then retested to determine the optimal molar ratios of Class I to Class II solutes. Of these three solutions, a raffinose:TMAO molar ratio of 1.6:1 resulted in the highest percentage of survival of embryos (see FIG. 5). The second highest percentage of survival was obtained with a trehalose:TMAO molar ratio of 1.3:1. The third highest percentage of survival was obtained with a raffinose:betaine molar ratio of 1.4:1.

Figure 6:
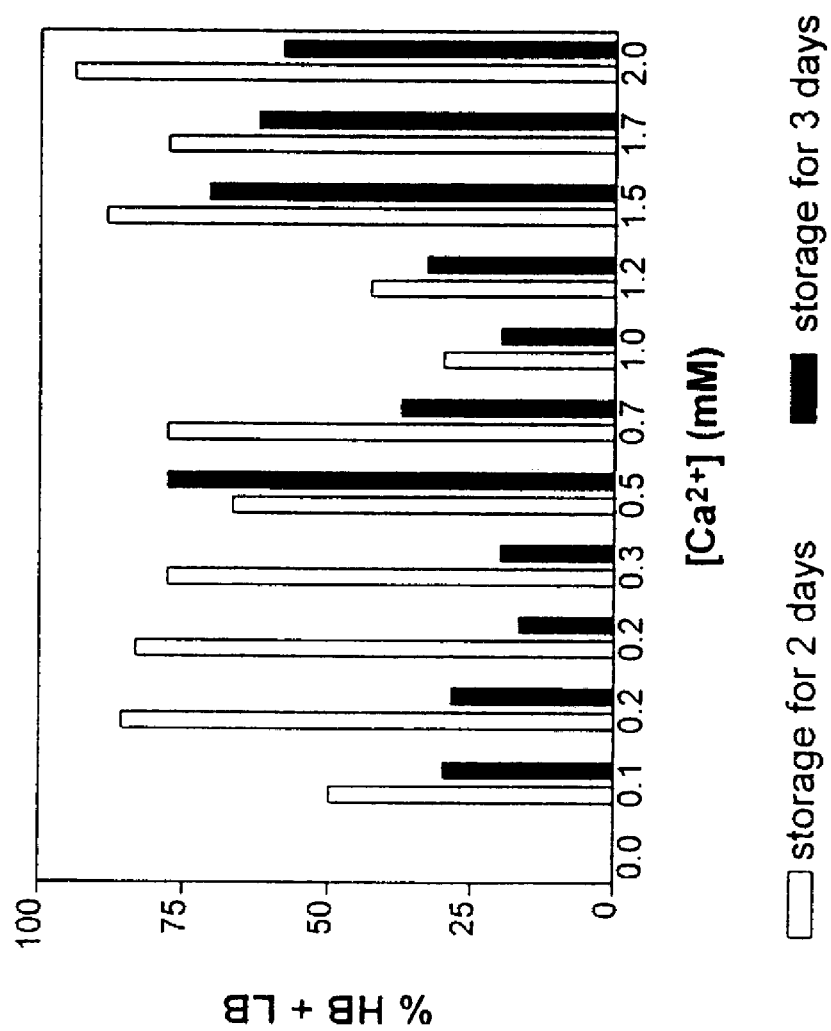
FIG. 6 shows the $Ca^{2+}$ dependence of mouse embryo survival following storage in raffinose/TMAO at 4° C. for 2 and 3 days.

The percentage of embryos hatching following storage in solutions containing a 1.6:1 molar ratio of raffinose to TMAO and varying concentrations of $Ca^{2+}$ is shown in FIG. 6. It was found that $Ca^{2+}$ is required for embryo preservation, with a non-linear concentration dependence. A $CaSO_4$ concentration of 1.75 mM was subsequently used in all solutions and with most biological materials. One exception was that of isolated platelets which were found to survive best in $Ca^{2+}$-free solutions.

Figure 7B:
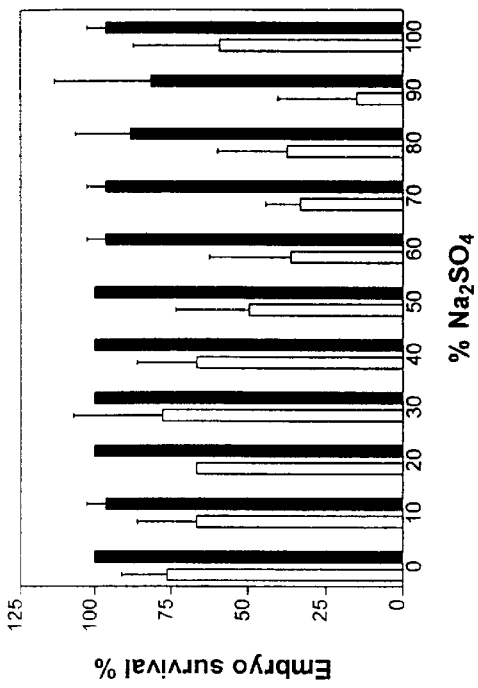
FIGS. 7A, B and C show the survival of mouse embryos following storage for 1, 2 and 3 days, respectively, at 4° C. in mixtures of raffinose/TMAO and $Na_2SO_4$, with 1.75 mM $CaSO_4$.
FIG. 7D shows the mean and SEM of survival of mouse embryos following 1, 2, 3 and 4 days of storage in Solution 70/30 at various osmolalities.
Figure 7A:
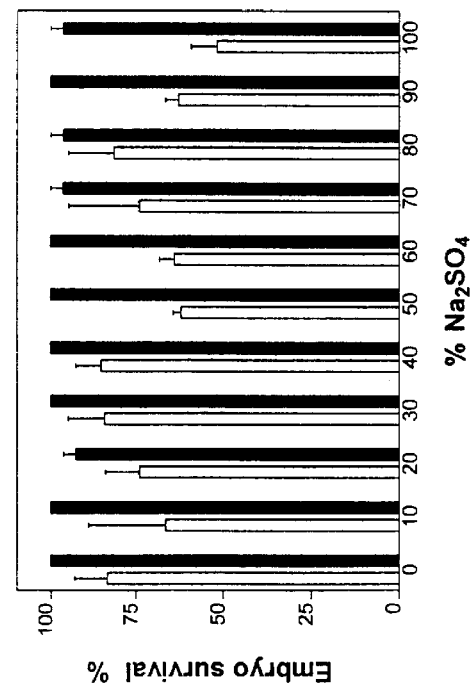
Figure 7C:
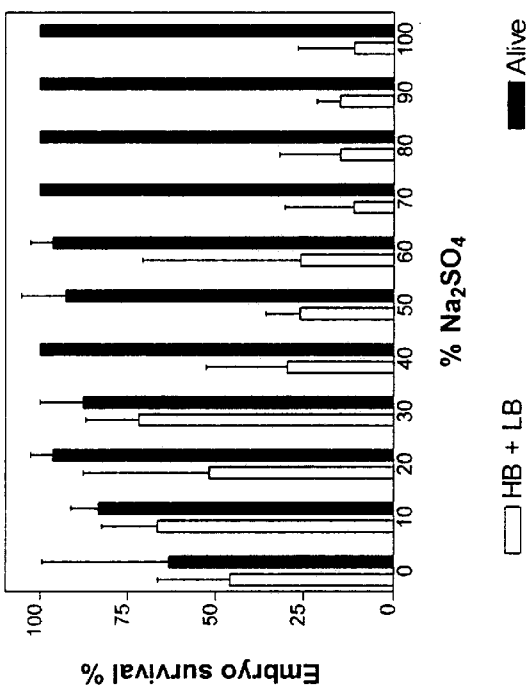
Figure 7D:
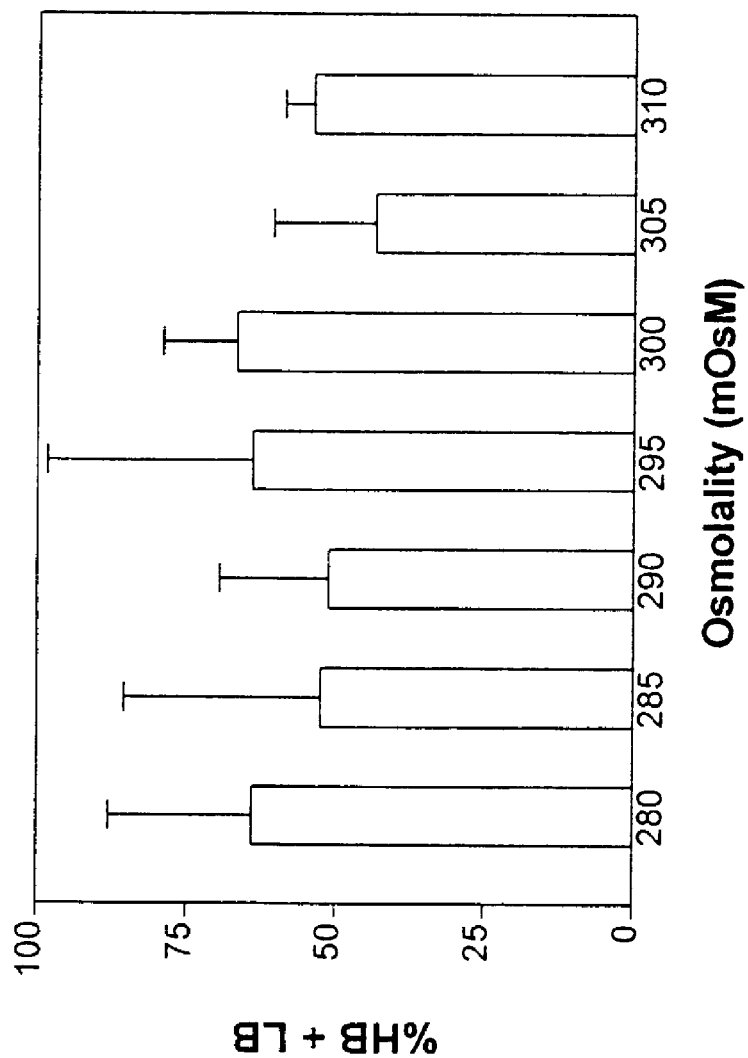

A raffinose/TMAO 1.6:1 solution with 1.75 mM $CaSO_4$ was then mixed in different proportions with a solution of 0.30 OsM $Na_2SO_4$ containing 1.75 mM $CaSO_4$. The percentage of mouse embryos hatching in culture following storage in these solutions for 1, 2 and 3 days are shown in FIGS. 7(i)A, B and C, respectively. The highest percentage of hatched embryos was obtained with 70% raffinose/TMAO (1.6:1), 30% $Na_2SO_4$ and 1.75 mM $CaSO_4$ (hereinafter referred to as Solution 70/30). FIG. 7(ii) shows the survival of embryos following storage in Solution 70/30 of various osmolalities. The optimal osmolality appears to be close to 300 mOsM but not to be of critical importance. Solution 70/30 was subsequently used for many applications and proved to be the most effective storage solution for bone marrow stem cells, hearts, red blood cells and osteoblasts. Solution 70/30 without $Ca^{2+}$ was found to be the most effective solution for the preservation of platelets.

EXAMPLE 2

As described below, survival of mouse embryos in storage was found to be greatly enhanced by pretreatment with either a Class II solute or sodium butyrate.

Figure 8B:
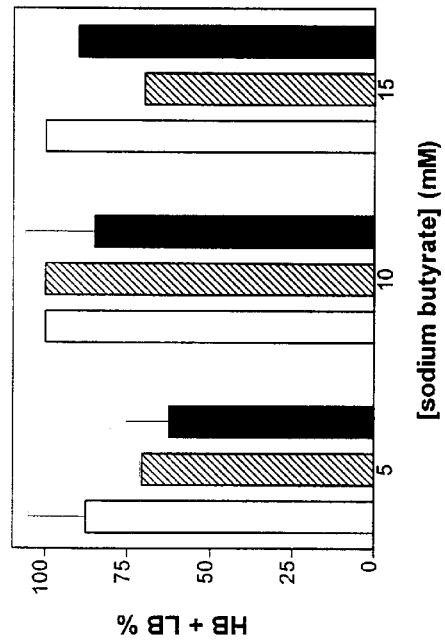
FIGS. 8A, B and C show the percentage of mouse embryos reaching the late blastocyst stage following storage for 1, 2 and 3 days, respectively, at 4° C. in Solution 70/30 after pretreatment with 5, 10 or 15 mM sodium butyrate in PBS at room temperature for 10, 20 or 30 minutes.
FIGS. 8D, E and F show the percentage of mouse embryos alive following storage for 1, 2 and 3 days, respectively, at 4° C. in Solution 70/30 after pretreatment with 5, 10 or 15 mM sodium butyrate in PBS at room temperature for 10, 20 or 30 minutes.
Figure 8A:
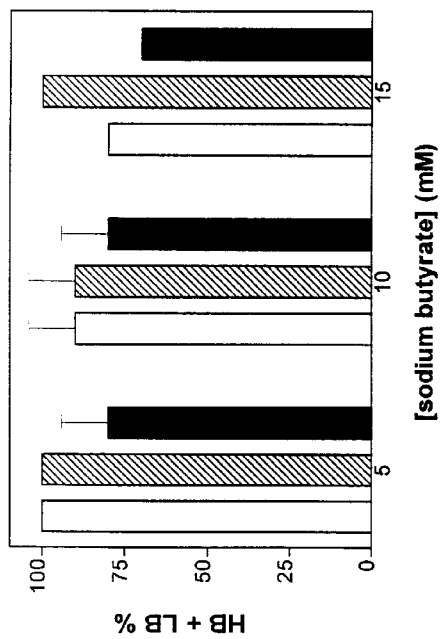
Figure 8C:
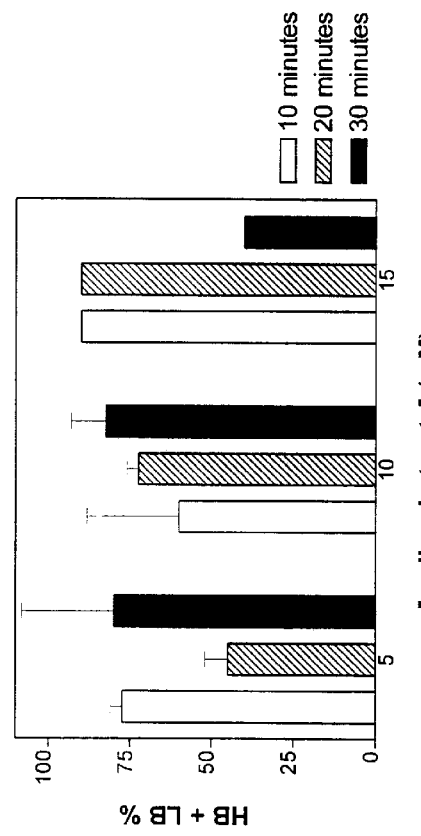
Figure 8E:
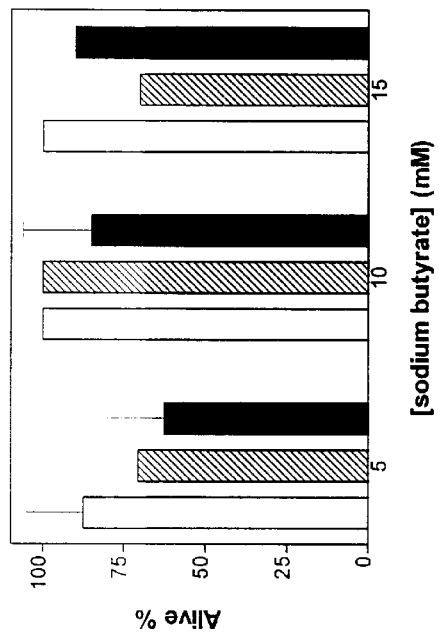
Figure 8D:
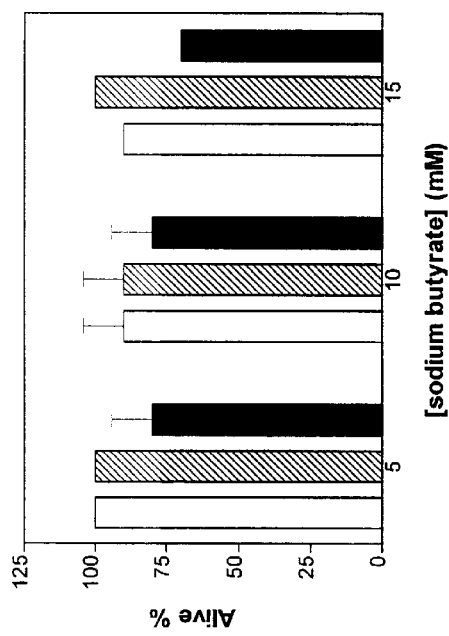
Figure 8F:
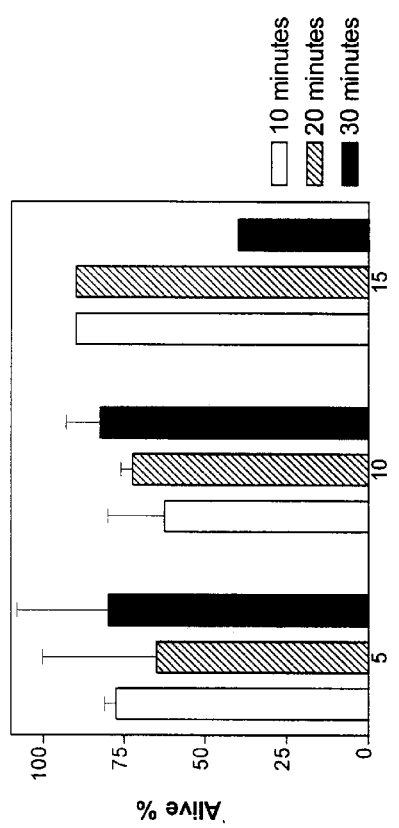
Figure 9:
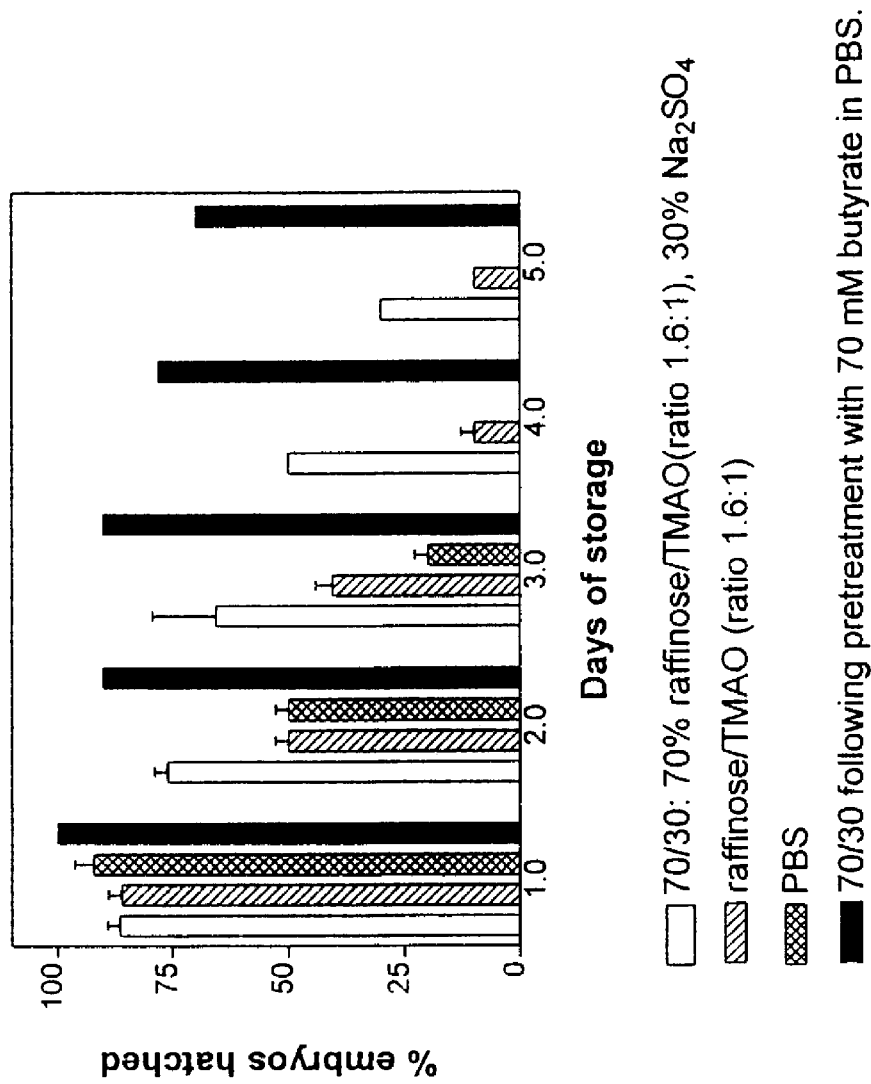
FIG. 9 shows the survival of mouse embryos following storage at 4° C. in PBS, raffinose/TMAO (ratio 1.6:1), or Solution 70/30, with and without pretreatment with 70 mM butyrate in PBS.

Mouse embryos were incubated with either sodium butyrate or a Class II solute at either room temperature, 30° C. or 4° C. prior to storage in Solution 70/30 for up to five days at 4° C. Many different combinations of concentrations of sodium butyrate (5–70 mM) and times of pretreatment (5–30 minutes) at room temperature gave significantly improved storage times. Sodium butyrate replaced sodium chloride at the same concentration in PBS. FIGS. 8A, B and C show the percentage of mouse embryos hatching after 1, 2 and 3 days, respectively, in storage following pretreatment with sodium butyrate at concentrations of 5, 10 or 15 mM for either 10, 20 or 30 minutes. FIGS. 8D, E and F show the percentage of mouse embryos alive after 1, 2 and 3 days, respectively, in storage following pretreatment with sodium butyrate at concentrations of 5, 10 or 15 mM for either 10, 20 or 30 minutes. Pretreatment with sodium butyrate allowed up to 80% of embryos to hatch following three days of storage in Solution 70/30. After 5 days of storage in Solution 70/30 following pretreatment with higher concentrations of sodium butyrate, up to 70% of embryos hatched compared to 2% with no pretreatment (see FIG. 9). Embryos stored in PBS without pretreatment lasted no longer than 3 days. Pretreatment of embryos with PBS without butyrate resulted in significant loss of embryos. FIGS. 10A, B, C and D show the survival of mouse embryos after up to four days of storage in Solution 70/30 following pretreatment with 25 mM sodium butyrate for 5, 10 or 15 minutes at room temperature.

EXAMPLE 3

The efficacy of Solution 70/30 in the storage of whole blood was investigated as detailed below.

Whole blood was diluted 1:1 by volume with either plasma, $Ca^{2+}$-containing Solution 70/30 or $Ca^{2+}$-free Solution 70/30, and stored at 4° C. for periods of up to 28 days. In the presence of citrate-based anticoagulant solutions, platelets decreased to about 30% of their initial numbers in 18 days. When EDTA was used as the anticoagulant, platelet numbers stayed in the normal range, i.e. close to about 60% survival, in $Ca^{2+}$-free Solution 70/30 but not in $Ca^{2+}$-containing Solution 70/30 or plasma.

In the same tests, white cells survived little better than platelets in a citrate-based anticoagulant. Highest survival rates after 18 days were obtained when blood was collected into an EDTA containing bag and diluted 1:1 by volume with $Ca^{2+}$-containing Solution 70/30, compared to storage in either $Ca^{2+}$-free Solution 70/30 of plasma. This replaced the $Ca^{2+}$ necessary for white cell storage and avoided the harmful effects of citrate.

EXAMPLE 4

This example illustrates the efficacy of the preservation solutions of the present invention in storage of isolated platelets.

Figure 11:
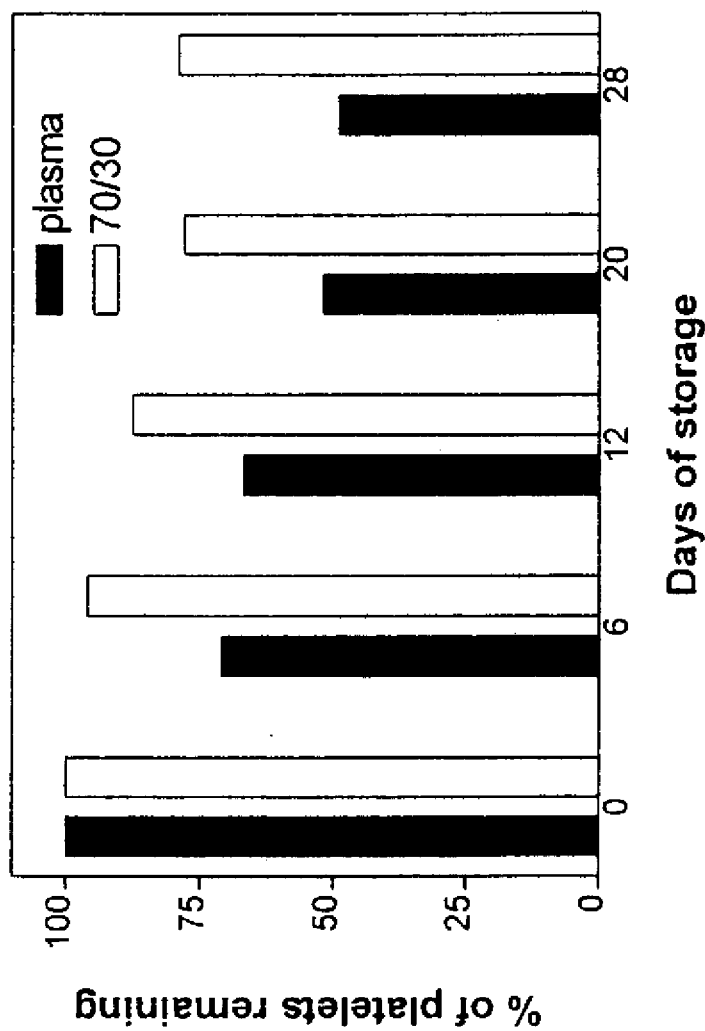
FIG. 11 shows the survival of platelets following storage at 4° C. in either plasma or $Ca^{2+}$-free Solution 70/30.

Blood was collected in EDTA and platelets isolated using standard centrifugation techniques. The final platelet-rich pellet was diluted into 50 ml of either plasma or $Ca^{2+}$- free Solution 70/30. FIG. 11 shows that 80% of platelets survived after 28 days of storage at 4° C. This survival rate after storage was significantly better than that in plasma and considerably better than the five days for which platelets are typically held at 21° C. The advantages of collection of blood in EDTA and avoidance of citrate, together with storage in $Ca^{2+}$-free Solution 70/30 at 4° C. are very clear.

EXAMPLE 5

This example illustrates the efficacy of solutions of the present invention for preservation of human bone marrow.

Bone marrow was collected in heparin from two different patients and diluted 1:1 by volume with solutions of the present invention or with a standard saline solution (Hanks buffered saline solution (HBSS), or saline-based murine culture medium (M-2)). The bone marrow was stored at 4° C. for periods ranging up to 28 days, at which time the white cell count and viability, number of colony forming units, and populations of CD34 and CD45 cells were determined.

Figure 12A:
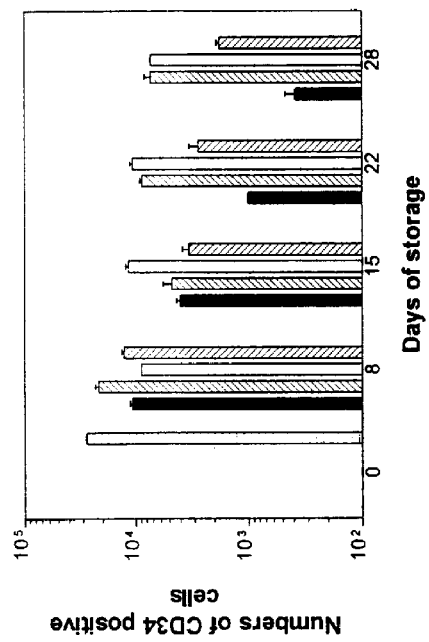
FIGS. 12A, B and C show the number of CD45- and CD34-positive cells and colony forming units, respectively, in bone marrow from patient 1 following storage in either Hanks buffered saline solution, raffinose/TMAO, trehalose/betaine or Solution 70/30.
Figure 12B:
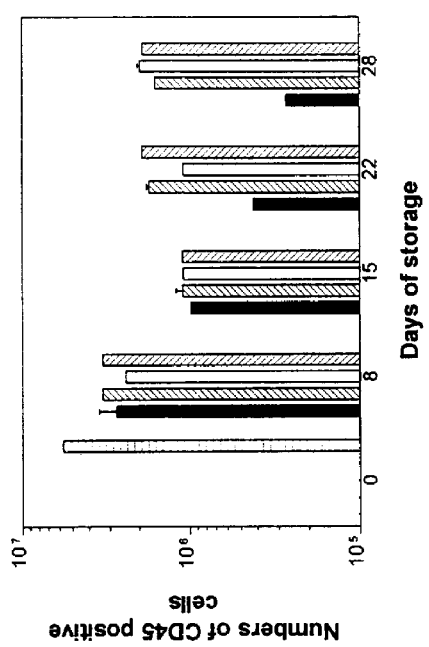
Figure 12C:
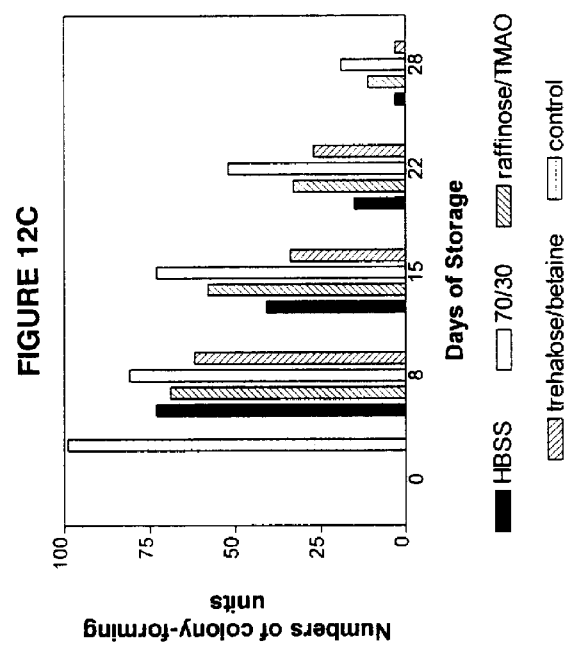

FIGS. 12A, B and C show the number of CD-45 positive and CD-34 positive cells and colony-forming units, respectively, from bone marrow harvested from patient 1 and stored in the inventive solutions for up to 28 days. FIGS. 13A, B and C show the number of colony-forming units, CD45-positive and CD34-positive cells, respectively, from bone marrow harvested from patient 2 and stored at 4° C. in preservative and control solutions. Raffinose/TMAO had a molar ratio of 1.6:1 and the trehalose/betaine solution had a molar ratio of 1.4:1. Solution 70/30 was particularly effective in preserving bone marrow stem cells, the numbers of colony-forming units, CD45 and CD34-positive cells being much higher than they were in any of the control solutions, with the relative improvement increasing with time. FIGS. 13A, B and C demonstrate that the number of colony forming units, CD34-positive cells and CD-45 positive cells was significantly higher following storage in Solution 70/30 compared to storage in the saline medium M-2. The ability to store bone marrow for periods of 2–3 weeks without freezing is particularly advantageous in bone marrow transplants, since it avoids the toxicity associated with the use of DMSO in cryopreservation and allows time for a therapeutic regime, such as whole-body radiation, before re-infusion.

EXAMPLE 6

The efficacy of the inventive solutions for preservation of murine bone marrow cells was determined as follows.

Murine bone marrow was harvested directly into Solution 70/30 or into PBS. The resulting solutions were stored either at 4° C. or –80° C. FIG. 14A shows that murine bone marrow stored in Solution 70/30 at 4° C. showed 28% recovery after 14 days, with no bone marrow cells stored at 4° C. in PBS for 14 days surviving. Bone marrow frozen in Solution 70/30 at –80° C. showed 20% recovery after 8 and 14 days, whereas no bone marrow cells frozen in PBS at –80° C. for 2, 6, 8 and 14 days survived.

Figure 14B:
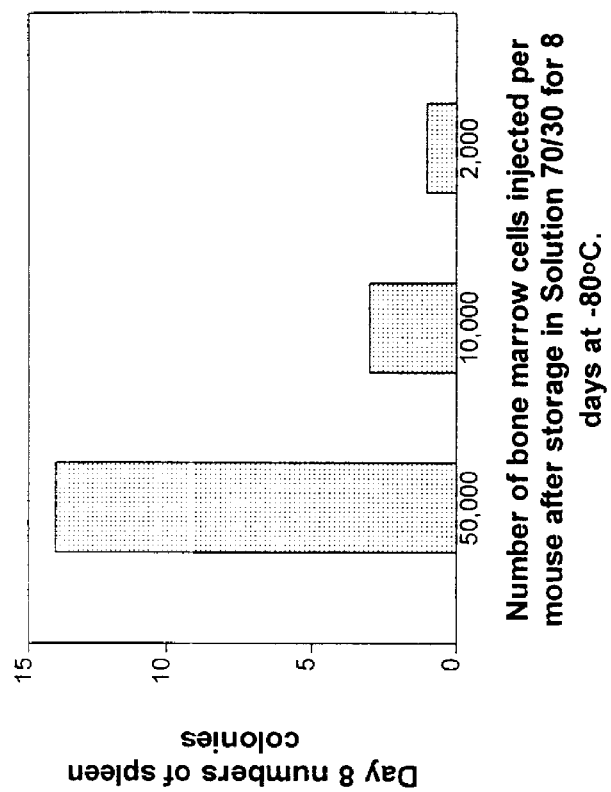
FIG. 14B shows the number of cell colonies found in spleens of lethally irradiated mice 8 days after injection of thawed murine bone marrow cells which had been stored in Solution 70/30 for 8 days at −80° C.
Figure 14A:
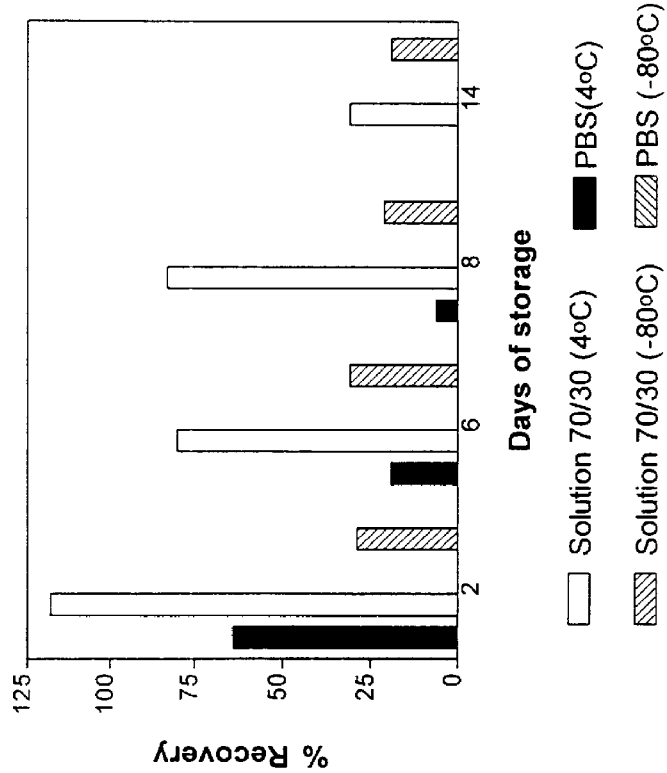
FIG. 14A shows the percentage recovery of murine bone marrow cells stored in PBS or Solution 70/30 at either 4° C. or −80° C.

FIG. 14B shows that murine bone marrow frozen in Solution 70/30 at –80° C. for 8 days, thawed and then injected into lethally irradiated (1000R) syngeneic mice, developed spleen colonies when analyzed eight days after injection. Mice injected with 50,000 bone marrow cells developed sixteen colonies, mice injected with 10,000 cells developed four colonies, and one mouse injected with 2000 bone marrow cells developed two colonies.

Figure 15:
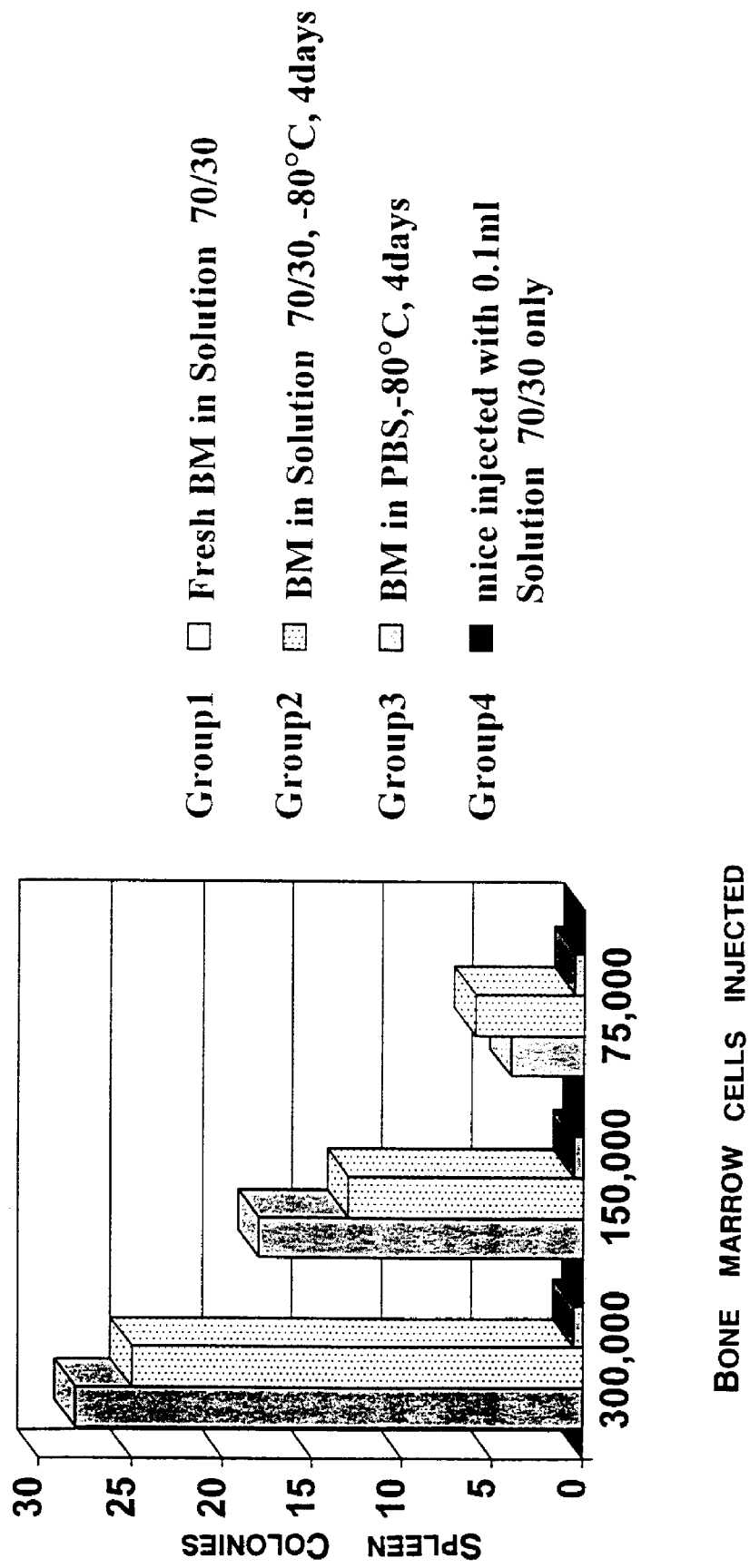
FIG. 15 shows the number of cell colonies found in spleens of lethally irradiated mice 9 days after injection with either fresh murine bone marrow cells, murine bone marrow cells stored in Solution 70/30 at −80° C. for 4 days, murine bone marrow cells stored in PBS at −80° C. for 4 days, or 0.1 ml Solution 70/30 with no cells.
Figure 16:
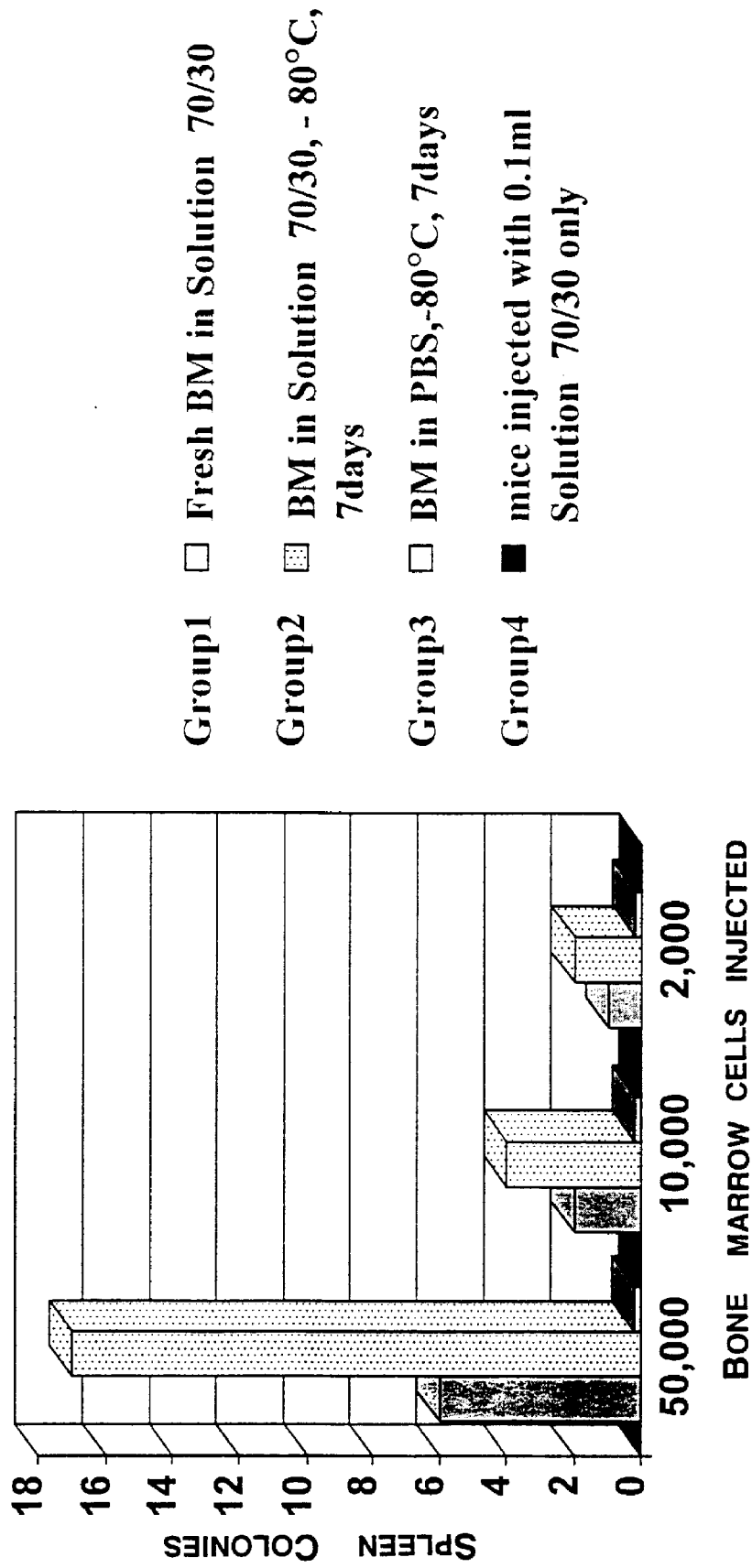
FIG. 16 shows the number of cell colonies found in spleens of lethally irradiated mice 10 days after injection with either fresh murine bone marrow cells, murine bone marrow cells stored in Solution 70/30 at −80° C. for 7 days, murine bone marrow cells stored in PBS at −80° C. for 7 days, or 0.1 ml Solution 70/30 with no cells.
Figure 17:
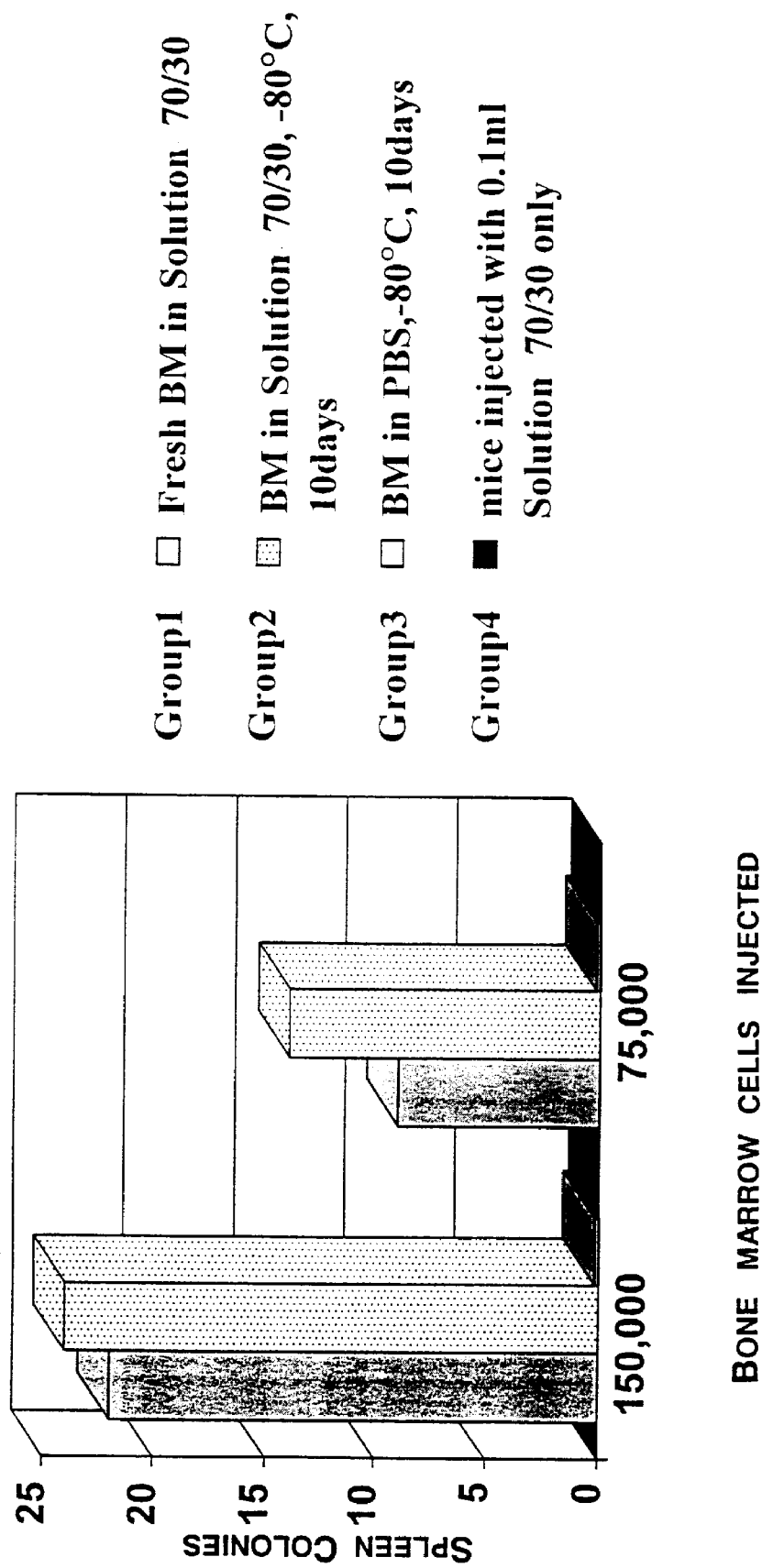
FIG. 17 shows the number of cell colonies found in spleens of lethally irradiated mice 10 days after injection with either fresh murine bone marrow cells, murine bone marrow cells stored in Solution 70/30 at −80° C. for 10 days, murine bone marrow cells stored in PBS at −80° C. for 10 days or 0.1 ml Solution 70/30 with no cells.

FIGS. 15, 16 and 17 show the effects of freezing murine bone marrow at –80° C. in Solution 70/30 or phosphate-buffered saline (PBS) for 4–10 days on the survival of haematopoietic stem cells, as determined by the ability to form spleen colonies 9–10 days after injection into lethally irradiated mice. Bone marrow was collected from the femurs of donor 6–8 week old BALB/c mice directly into Solution 70/30, or into phosphate-buffered saline (PBS) in 15 ml sterile polypropylene centrifuge tubes. These tubes were placed in a freezer at –80° C. After 4 days (FIG. 15), 7 days (FIG. 16) and 10 days (FIG. 17) tubes containing bone marrow in Solution 70/30 or PBS were removed from the freezer and thawed at room temperature. Viable cell numbers were determined.

To determine haematopoietic stem cell activity in the frozen and thawed bone marrow, recipient BALB/c mice (6–10 weeks old) were lethally irradiated and divided into four groups, each group containing four mice. In addition, fresh bone marrow was collected from healthy donor BALB/c mice in Solution 70/30. The four groups of irradiated recipient mice were injected intravenously with 0.1 ml of the following:

Group 1: fresh bone marrow cells collected directly in Solution 70/30;

Group 2: identical numbers of bone marrow cells collected in Solution 70/30 and frozen at –80° C.;

Group 3: identical numbers of bone marrow cells collected in PBS and frozen at –80° C.;

Group 4: Solution 70/30 lacking bone marrow cells.

The number of bone marrow cells injected is shown in each figure. The data demonstrate that murine haematopoietic stem cells survive freezing in Solution 70/30 at –80° C. for periods of up to 10 days and retain in vivo spleen colony forming properties.

The following murine and human haematopoietic tumor cell lines were resuspended in Solution 70/30 and frozen at –80° C. for periods of from 2 to 10 days: P3 (murine plasmacytoma); SP2/0 (murine plasmacytoma); EL4 (murine T cell lymphoma); Jurkat (human T cell lymphoma); HL60 (human monocytic tumor); and K562 (human early haematopoietic tumor). Upon thawing at room temperature and analysis for viable cells, either by uptake of trypan blue, or by the ability to grow in mammalian tissue culture medium supplemented with fetal bovine serum at 37° C., no cells were observed to survive freezing at –80° C.

The ability of the inventive solutions to purge murine bone marrow of leukemic cells was demonstrated as follows. Fresh bone marrow cells from BALB/c mice were collected in Solution 70/30 at a concentration of $10^7$ cells per ml. SP2/0 cells were also prepared in Solution 70/30 at a concentration of $10^7$ cells per ml. Three groups of cells were prepared for freezing at –80° C.:

Group 1: bone marrow cells in Solution 70/30;

Group 2: a mixture of equal parts of bone marrow and SP2/0 cells in Solution 70/30; and Group 3: SP2/0 cells alone in Solution 70/30.

Figure 18:
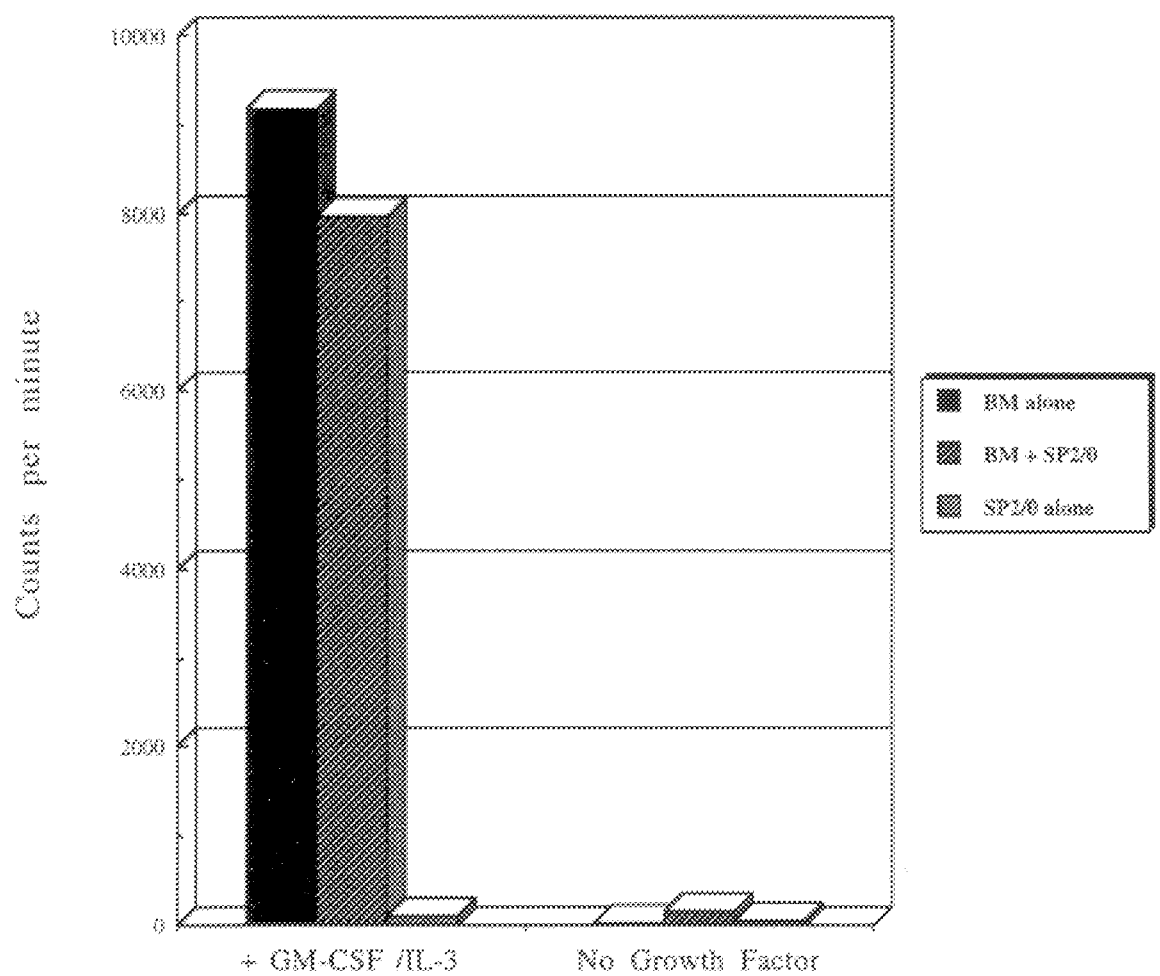
FIG. 18 shows the uptake of tritiated thymidine by murine bone marrow cells, leukemic SP2/0 cells, and a mixture of murine bone marrow cells and SP2/0 cells, following storage in Solution 70/30 at −80° C. for 4 days.

After 4 days, cells were thawed at room temperature, collected by centrifugation and resuspended in mammalian tissue culture medium containing 5% fetal bovine serum, 20 ng/ml of murine granulocyte-macrophage colony stimulating factor (GM-CSF) and 20 ng/ml of Interleukin-3 (IL-3). Cells were incubated at 37° C. in an incubator gassed with 10% $CO_2$ in air. After 4 days, cells were incubated with 1 μC per ml of radioactive thymidine for 24 hours, and uptake was measured and expressed as counts per minute. As shown in FIG. 18, bone marrow cells alone survived storage in Solution 70/30 at –80 ° C., whereas the SP2/0 cells did not survive storage under these conditions. In the mixture of bone marrow and SP2/0 cells, only the bone marrow cells survived.

EXAMPLE 7

The efficacy of the inventive solutions for preservation of hearts was determined as follows.

Figure 19:
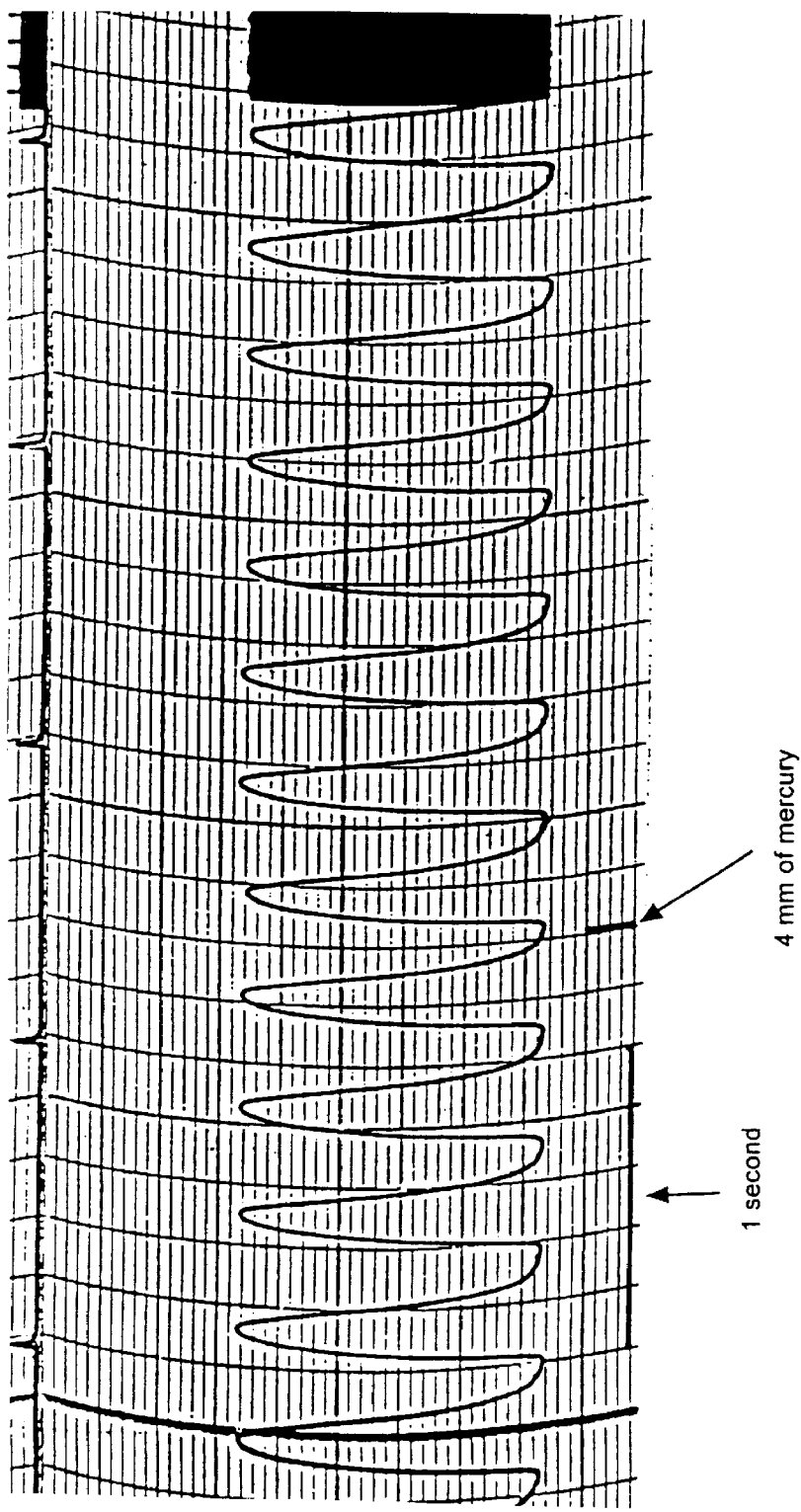
FIG. 19 shows a trace from a pressure transducer for a rat heart following storage for 4 hours at 4° C. in Solution 70/30.

Rat hearts were surgically removed and perfused through the aorta with either Solution 70/30 or raffinose/TMAO (molar ratio 1.6:1) at 4° C., during which time the heart rate fell from about 300 beats per minute to about 180 beats per minute. The hearts were then stored in the same solution for between 4 to 24 hours, during which time the hearts stopped beating. The hearts were subsequently remounted on a cannula and reperfused with Krebs solution initially at room temperature rising to 37° C. over 20 minutes. Using only gravity feed of the perfusing solutions, recovery of hearts after 4 hours of storage was excellent, with both heart rate and developed pressure in the normal range (heart rate 170 beats/minute, pressure 98 mm mercury; FIG. 19). When pumps were used in perfusion, variable results were obtained. In general, the pressure exerted by the pump on the heart was found to be damaging, with the damage often being irreversible.

Storage for periods longer than 4 hours was achieved by pretreating the heart with 25 mM taurine in Krebs solution for 10 minutes at 38° C. before perfusion with cold Solution 70/30 or raffinose/TMAO and storage at 4° C. With only gravity feed for the initial perfusion and the reperfusion, hearts stored for 24 hours recovered heart rate in the normal range and pressure approximately half the normal level. Subsequent experiments showed that pretreatment with taurine could be avoided by adding approximately 0.2 mM taurine to the storage solution to prevent efflux of endogenous taurine. The results obtained using the storage solutions of the present invention compare favorably with the prior art technique of preserving hearts in cold saline-based media, wherein the heart can only be stored for 5 hours or less due to unacceptable deterioration of biological function. Storage of a heart for 24 hours without deterioration would allow time for its transport for transplantation worldwide.

EXAMPLE 8

Figure 20:
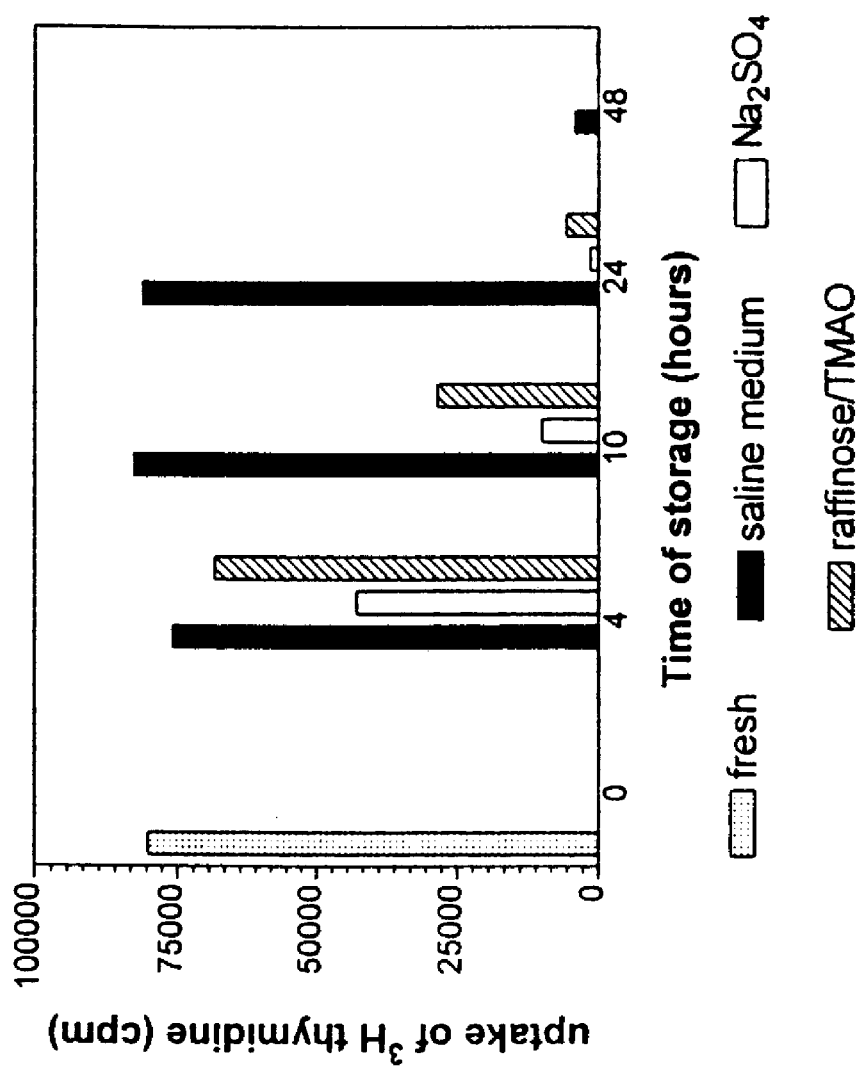
FIG. 20 shows the proliferation of Jurkat cells (acute T-cell leukemia) assessed by uptake of tritiated thymidine, following storage at 4° C. in saline or in preservation solutions of the present invention for up to 48 hours.
Figure 21:
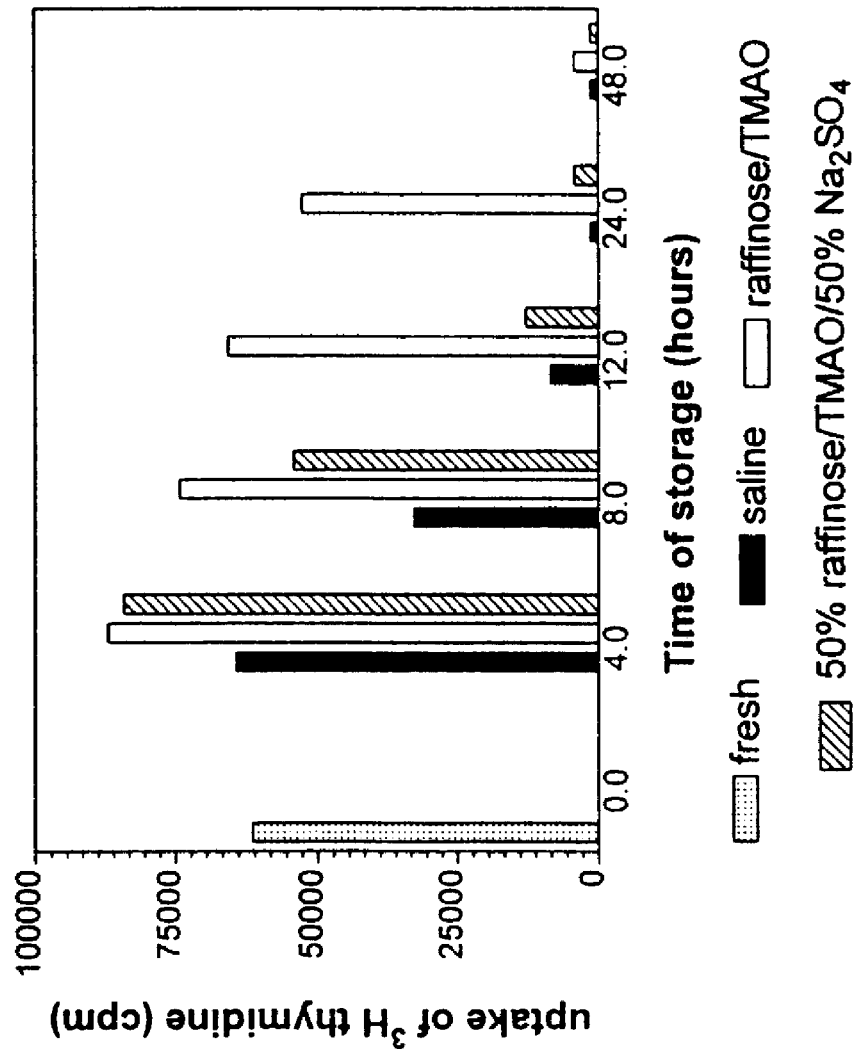
FIG. 21 shows proliferation of K562 chronic myelogenous leukemia cells assessed by uptake of tritiated thymidine following storage at 4° C. in saline or in preservation solutions of the present invention for up to 48 hours.

The efficacy of the inventive solutions for the preservation of various tumor cell lines, including the human lymphocytic leukemia Jurkat and K562 chronic myelogenous leukemia cell lines was tested using the solutions tested for preservation of human bone marrow described above in Examples 5 and 6. In contrast to the bone marrow progenitor cells, the tumor cell lines survived only two days in the inventive solutions before complete cell death (see FIGS. 20 and 21). Thus, storage of bone marrow in the preservative solutions of the present invention for periods of greater than three days would purge the bone marrow of leukemic cells while maintaining the viability of the bone marrow.

EXAMPLE 9

The efficacy of the inventive solutions in the preservation of osteoblasts was demonstrated as follows.

Figure 22:
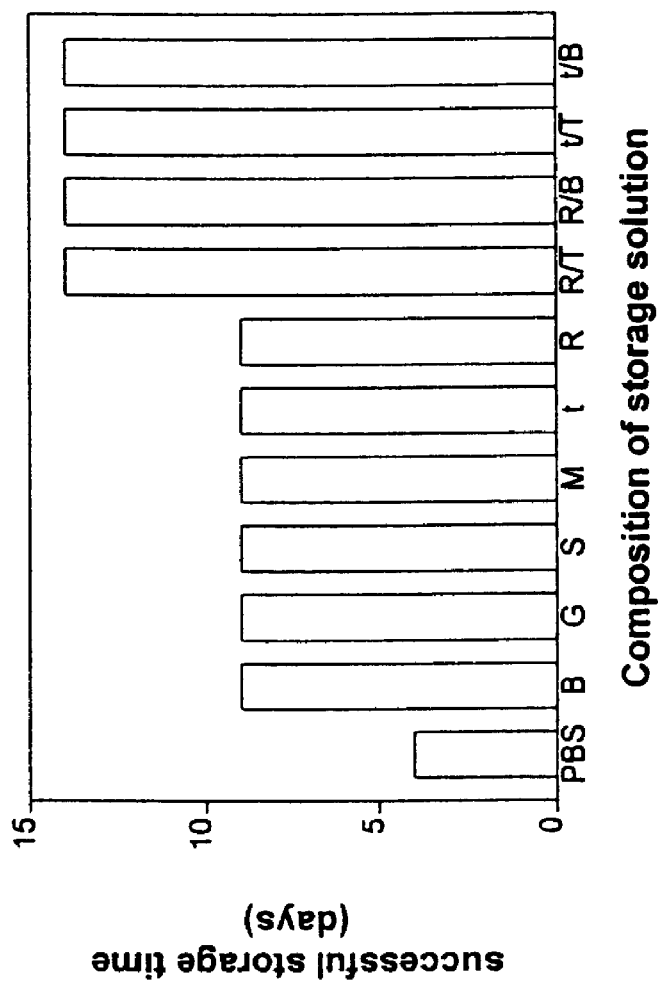
FIG. 22 shows proliferation to confluence of murine osteoblasts following storage at 4° C. in PBS and various preservation solutions of the present invention.

Mouse osteoblasts were dissected out and grown to near confluence in D-MEM culture medium at 38° C. They were then dispersed with trypsin in a $Ca^{2+}$- and $Mg^{2+}$-free phosphate buffered saline and re-seeded into D-MEM. After further culture, the medium was removed by aspiration and replaced with one of the following solutions: PBS, betaine, galactose, sorbitol, mannose, trehalose, raffinose, raffinose/TMAO (ratio 1.6:1), raffinose/betaine (ratio 1.6:1), trehalose/TMAO (ratio 1.6:1) and trehalose/betaine (ratio 1.6:1). After storage at 4° C. for varying time intervals, the storage solution was aspirated off and replaced with D-MEM. A successful storage was one in which osteoblasts subsequently grew to confluence. As shown in FIG. 22, osteoblasts survived storage in the inventive solutions for much longer periods than in PBS. Osteoblasts were found to be more tolerant of fluctuations in osmolality than were embryos.

EXAMPLE 10

Figure 23:
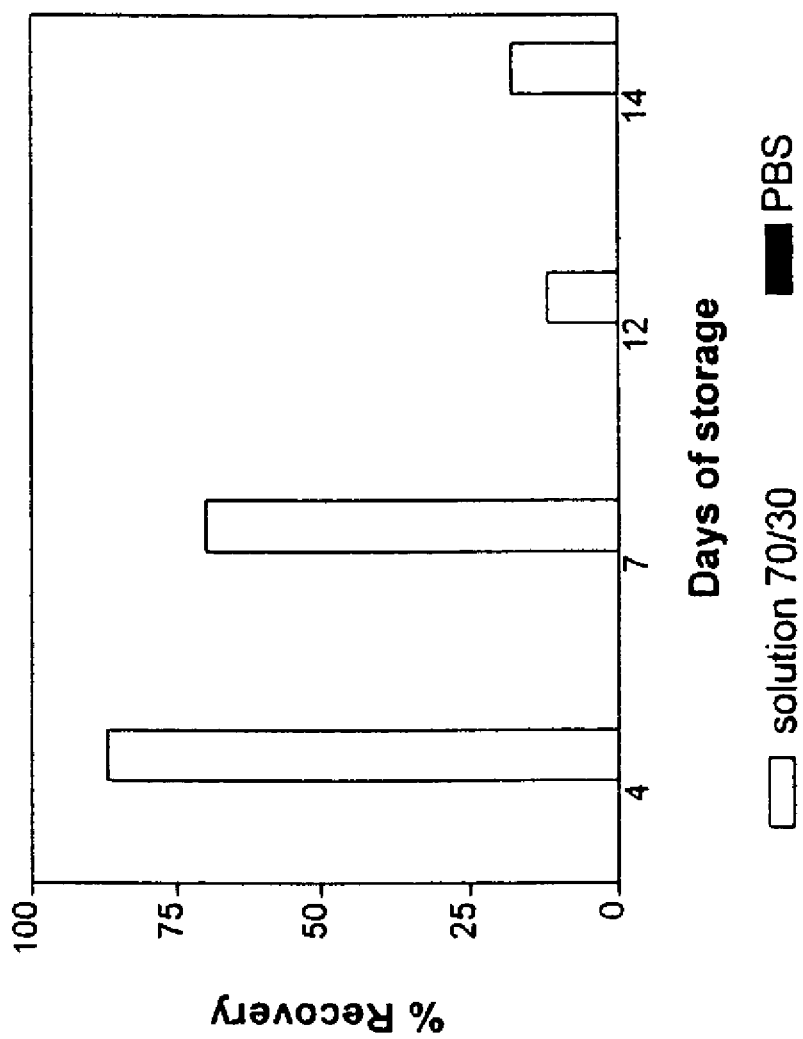
FIG. 23 shows the percentage recovery of a murine keratocyte cell line T7T after storage in PBS or Solution 70/30.

The efficacy of the inventive solutions in the preservation of murine T7T keratinocyte tumor cell line was investigated as follows. The culture medium was removed from adherent cultures of T7T growing in D-MEM supplemented with 5% serum by aspiration and replaced with PBS or Solution 70/30 prior to storage at 4° C. After 4, 7, 12 and 14 days these solutions were removed, the adherent cells removed by 25 trypsinization and recovery determined. FIG. 23 shows that no viable T7T cells survived in PBS but viable T7T cells were recovered following up to 14 days of storage in Solution 70/30.

EXAMPLE 11

Figure 24:
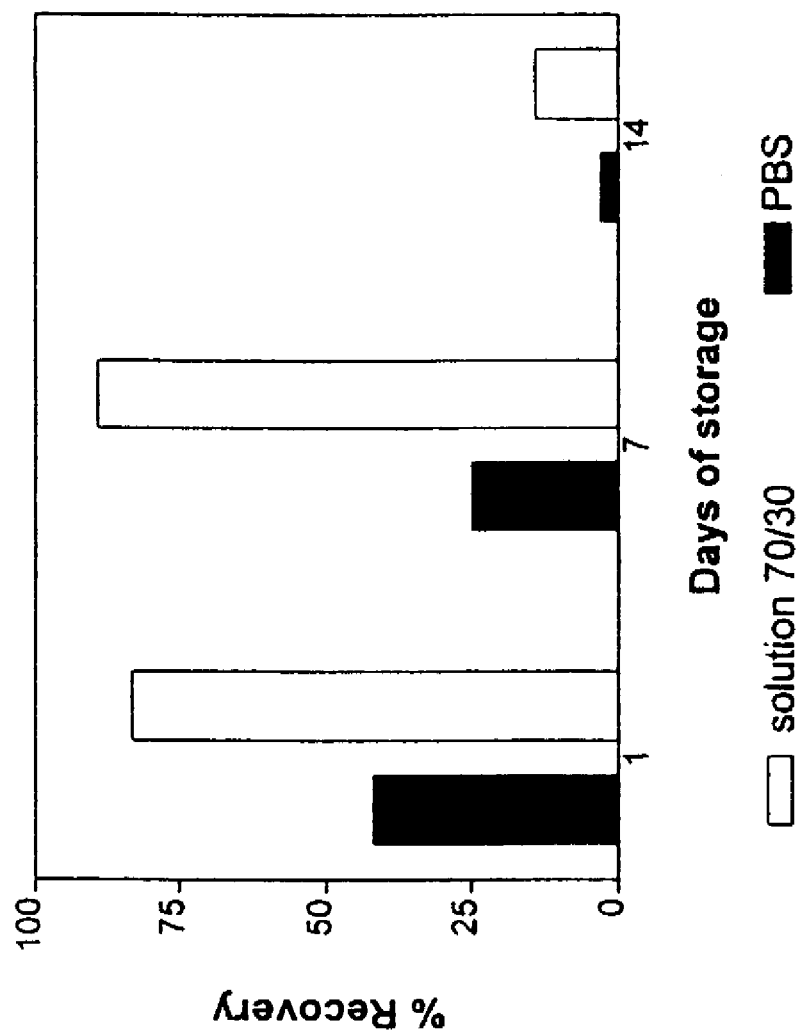
FIG. 24 shows the percentage recovery of murine 3T3 fibroblasts after storage in PBS or Solution 70/30.

The efficacy of the inventive solutions in the preservation of murine 3T3 fibroblast cells was demonstrated as follows. Adherent cultures of 3T3 cells growing in D-MEM supplemented with 5% serum had the medium removed by aspiration and replaced with PBS or Solution 70/30 prior to storage at 4° C. After 1, 7 and 14 days, these solutions were removed, the adherent cells were removed by trypsinization and recovery was determined. As shown in FIG. 24, no viable 3T3 cells survived in PBS but viable 3T3 cells were recovered after up to 14 days of storage in Solution 70/30.

Although the present invention has been described in terms of specific embodiments, changes and modifications can be carried out without departing from the scope of the invention which is intended to be limited only by the scope of the appended claims.

We claim:

1. A method for preserving the viability of a biological material comprising the steps of:
    (a) contacting the biological material with a solution comprising raffinose and trimethyl amine oxide in a molar ratio of about 1.1 to 1 to about 2.0 to 1, wherein the solution is substantially isotonic with the biological material to be preserved and is substantially free of iodide, dihydrogen phosphate, bicarbonate, nitrate and bisulfate; and
    (b) storing the biological material.

2. The method of claim 1, wherein the raffinose and trimethyl amine oxides are present in a molar ratio of about 1.4 to 1 to about 1.8 to 1.

3. The method of claim 1, wherein the solution further comprises calcium ions.

4. The method of claim 3, wherein the calcium ions are from a compound selected from the group consisting of calcium sulfate and calcium chloride.

5. The method of either of claims 1 and 3, wherein the solution further comprises sodium sulfate.

6. A method for preserving the viability of a biological material comprising the steps of:
    (a) contacting the biological material with a solution comprising trehalose and trimethyl amine oxide in a molar ratio of about 1.1 to 1 to about 1.4 to 1, wherein the solution is substantially isotonic with the biological material to be preserved and is substantially free of iodide, dihydrogen phosphate, bicarbonate, nitrate and bisulfate; and
    (b) storing the biological material.

7. The method of claim 6, wherein the solution further comprises calcium ions.

8. The method of claim 7, wherein the calcium ions are from a compound selected from the group consisting of calcium sulfate and calcium chloride.

9. The method of either of claims 6 and 7, wherein the solution further comprises sodium sulfate.

10. A method for preserving the viability of a biological material comprising the steps of:
    (a) contacting the biological material with a solution comprising raffinose and betaine in a molar ratio of about 1.4 to 1 to about 1.6 to 1, wherein the solution is substantially isotonic with the biological material to be preserved and is substantially free of iodide, dihydrogen phosphate, bicarbonate, nitrate and bisulfate; and
    (b) storing the biological material.

11. The method of claim 10, wherein the solution further comprises calcium ions.

12. The method of claim 11, wherein the calcium ions are from a compound selected from the group consisting of calcium sulfate and calcium chloride.

13. The method of either of claims 10 and 11, wherein the solution further comprises sodium sulfate.

14. A method for preserving the viability of a biological material comprising the steps of:
  (a) contacting the biological material with a solution comprising trehalose and betaine in a molar ratio of about 1.4 to 1 to about 1.6 to 1, wherein the solution is substantially isotonic with the biological material to be preserved and is substantially free of iodide, dihydrogen phosphate, bicarbonate, nitrate and bisulfate; and
  (b) storing the biological material.

15. The method of claim 14, wherein the solution further comprises calcium ions.

16. The method of claim 15, wherein the calcium ions are from a compound selected from the group consisting of calcium sulfate and calcium chloride.

17. The method of either of claims 14 and 15, wherein the solution comprises sodium sulfate.

18. The method of any one of claims 1, 6, 10 and 14, wherein the biological material is a mammalian material and the solution has an osmolality of between about 280 to about 320 mOsM.

19. The method of any one of claims 1, 6, 10 and 14, wherein the biological material is a plant biological material and the solution has an osmolality of between about 70 to about 80 mOsM.

20. The method of any one of claims 1, 6, 10 and 14, wherein the biological material is a marine biological material and the solution has an osmolality of about 900 to about 1000 mOsM.

21. The method of any one of claims 1, 6, 10 and 14, wherein the biological material is selected from the group consisting of: heart, stem cells, bone marrow, embryos, platelets, blood, osteoblasts, fibroblasts and skin cells.

22. The method of any one of claims 1, 6, 10 and 14, wherein the biological material is stored at about 4° C.

23. The method of any one of claims 1, 6, 10 and 14, wherein the biological material is stored at a temperature of less than 4° C.

* * * * *